US007265149B2

(12) United States Patent
Ackermann et al.

(10) Patent No.: US 7,265,149 B2
(45) Date of Patent: Sep. 4, 2007

(54) INDOLYL DERIVATIVES

(75) Inventors: Jean Ackermann, Riehen (CH); Johannes Aebi, Basel (CH); Alfred Binggeli, Binningen (CH); Uwe Grether, Efringen-Kirchen (DE); Georges Hirth, Colmar (FR); Bernd Kuhn, Liestal (CH); Hans-Peter Maerki, Basel (CH); Markus Meyer, Neuenburg (DE); Peter Mohr, Basel (CH); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 126 days.

(21) Appl. No.: 11/074,474

(22) Filed: Mar. 8, 2005

(65) Prior Publication Data
US 2005/0203160 A1    Sep. 15, 2005

(30) Foreign Application Priority Data
Mar. 9, 2004    (EP)    .................... 04100958

(51) Int. Cl.
*A61K 31/4155* (2006.01)
*C07D 231/10* (2006.01)
(52) U.S. Cl. ...................... 514/414; 548/462
(58) Field of Classification Search ............... 548/462; 514/414
See application file for complete search history.

(56) References Cited
FOREIGN PATENT DOCUMENTS
WO    WO 03/074051 A1    9/2003
WO    WO2004063190    7/2004

OTHER PUBLICATIONS
Oliver, et. al., Proc Nat Acad Sci USA (2001) 98:5306-11.
Guerre-Millo, et. al., J Biol Chem (2000) 275:16638-16642.
Jones, et. al., J. Chem. Soc (1953), 2548.
E.J. Corey, et. al., J. Am. Chem. Soc (1987) 109, 5551-5553.
P.V. Ramachandran, et. al., Tetrahedron: Asymmetry (1994) 5, 1061-1074.
Nichols, et. al., (1998) Anal. Biochem. 257, 112-119.

*Primary Examiner*—Kamal A. Saeed
*Assistant Examiner*—Michael P. Barker
(74) *Attorney, Agent, or Firm*—George W. Johnston; Dennis P. Tramaloni; Samuel H. Megerditchian

(57) ABSTRACT

This invention relates to compounds of the formula I:

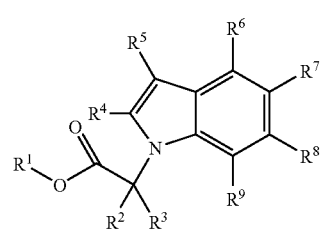

wherein one of $R^6$, $R^7$ and $R^8$ is

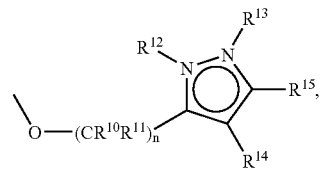

and $R^1$ to $R^{15}$ and n are as defined in the description, and all enantiomers and pharmaceutically acceptable salts and/or esters thereof. The invention further relates to pharmaceutical compositions containing such compounds, to a process for their preparation and to their use for the treatment and/or prevention of diseases which are modulated by PPAR δ and/or PPARα agonists.

22 Claims, No Drawings

INDOLYL DERIVATIVES

FIELD OF THE INVENTION

The present invention relates to novel indolyl derivatives of the formula I:

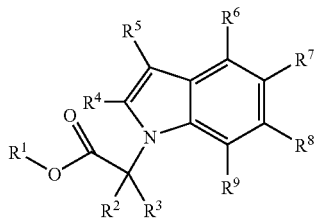

and enantiomers and pharmaceutically acceptable salts and esters thereof.

It has been found that the compounds of formula I are useful as lipid modulators and insulin sensitizers. In particular, the compounds of formula I are PPAR activators.

All documents cited or relied upon below are expressly incorporated herein by reference.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart.

There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol.

The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol >240 mg/dl is 37% in diabetic men and 44% in women. The respective rates for LDL-C >160 mg/dl are 31% and 44%, respectively, and for HDL-C <35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance.

A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients.

Therefore, new, more efficacious drugs with greater safety and lower side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306-11). Recent observations also suggest that there is a independent PPARα mediated effect on insulin-sensitzation in addition to its well known role in reducing triglycerides (Guerre-Millo et al; J Biol Chem 2000; 275: 16638-16642). Thus selective PPARα agonists, selective PPARδ agonists or PPAR α/δ agonists may show superior therapeutic efficacy without the side-effects such as the weight gain seen with pure PPARγ agonists.

SUMMARY OF THE INVENTION

In one embodiment of the present invention, compounds of the formula I

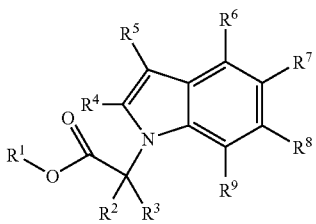

are provided.

In another embodiment of the present invention, provided is a method for the treatment and/or prevention of diseases which are modulated by PPARδ and/or PPARα agonists, the method having the step of administering a compound according to formula I to a human being or animal in need thereof.

DETAILED DESCRIPTION OF THE INVENTION

The novel compounds of the present invention are advantageous to those compounds known in the art. For example, and the compounds of the invention selectively activate PPARα or coactivate PPARδ and PPARα simultaneously and very efficiently, and with much improved pharmacokinetic properties. Therefore, these compounds combine the anti-dyslipidemic and anti-glycemic effects of PPARα and PPARδ activation with slightly no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ selective agonists and PPARδ and α coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy.

Preferred are the lower-alkoxy groups specifically exemplified herein.

The term "lower fluoroalkoxy" or "fluoro-$C_{1-7}$-alkoxy" refers to lower alkoxy groups as defined above which are mono- or multiply substituted with fluorine. Examples of lower fluoroalkoxy groups are e.g. —$OCF_3$, and —$OCH_2CF_3$.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoro-alkyl, lower-alkoxy, lower fluoro-alkoxy, aryl and/or aryloxy.

Preferred substituents are halogen, $CF_3$, $OCF_3$, lower-alkyl and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

A "lone pair" is a pair of electrons in the outermost shell of an atom, in particular a nitrogen atom, that are not used in bonding.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

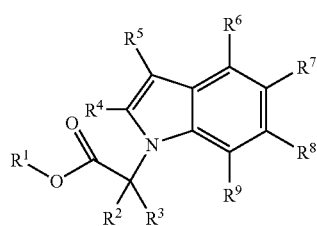

wherein
$R^1$ is hydrogen or $C_{1-7}$-alkyl;
$R^2$ and $R^3$ independently from each other are hydrogen, $C_{1-7}$-alkyl or $C_{1-7}$-alkoxy;
$R^4$ and $R^5$ independently from each other are hydrogen, $C_{1-7}$-alkyl,
$C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
$R^6$, $R^7$, $R^8$ and $R^9$ independently from each other are hydrogen, $C_{1-7}$-alkyl,
$C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

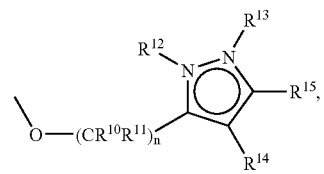

wherein
$R^{10}$ is hydrogen, $C_{1-7}$-alkyl, $C_{3-7}$-cycloalkyl or fluoro-$C_{1-7}$-alkyl;
$R^{11}$ is hydrogen, $C_{1-7}$-alkyl or $C_{1-7}$-alkoxy-$C_{1-7}$-alkyl;
one of $R^{12}$ or $R^{13}$ is hydrogen, $C_{1-7}$-alkyl, $C_{3-7}$-cycloalkyl, $C_{2-7}$-alkoxy-$C_{1-7}$-alkyl, $C_{2-7}$-alkenyl, $C_{2-7}$-alkinyl or fluoro-$C_{1-7}$-alkyl; and the other one is a lone pair;
$R^{14}$ is hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;
$R^{15}$ is aryl or heteroaryl;
n is 1, 2 or 3; and
all enantiomers and pharmaceutically acceptable salts and/or esters thereof.

Preferred compounds of formula I of the present invention are compounds of formula

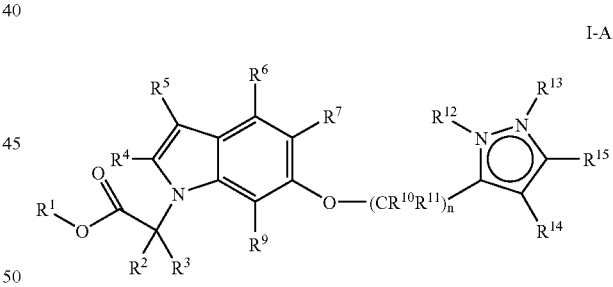

wherein
$R^1$ to $R^5$, $R^{10}$ to $R^{15}$ and n are as defined herein before;
$R^6$, $R^7$ and $R^9$ independently from each other are hydrogen, $C_{1-7}$-alkyl,
$C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

More preferred are those compounds of formula I-A in accordance with the present invention, wherein $R^6$, $R^7$ and $R^9$ are hydrogen.

Also preferred are compounds of formula I having the formula

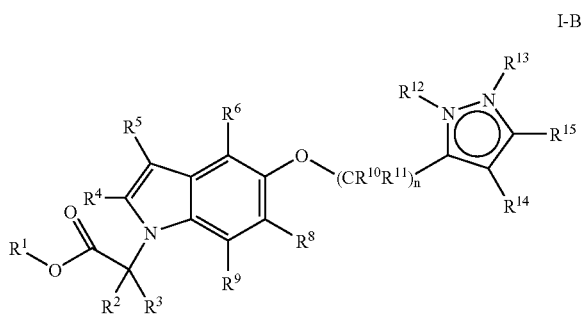

wherein
R¹ to R⁵, R¹⁰ to R¹⁵ and n are as defined herein before;
R⁶, R⁸ and R⁹ independently from each other are hydrogen, $C_{1-7}$-alkyl,
$C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

Especially preferred are compounds of formula I-B, wherein R⁶, R⁸ and R⁹ are hydrogen.

Further preferred compounds of formula I have the formula

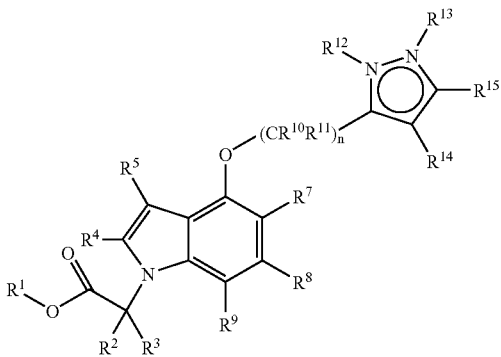

wherein
R¹ to R⁵, R¹⁰ to R¹⁵ and n are as defined herein before;
R⁷, R⁸ and R⁹ independently from each other are hydrogen, $C_{1-7}$-alkyl,
$C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

More preferred are those compounds of formula I-C, wherein R⁷, R⁸ and R⁹ are hydrogen.

Furthermore, compounds of formula I, wherein R¹ is hydrogen, are preferred.

Compounds of formula I, wherein R² and R³ independently from each other are hydrogen or methyl, are also preferred.

Also preferred are compounds of formula I, wherein at least one of R² and R³ is methyl.

Preferred are further compounds of formula I, wherein R⁴ is hydrogen.

Compounds of formula I, wherein R⁵ is hydrogen, $C_{1-7}$-alkyl or halogen, are also preferred.

The integer n is 1, 2 or 3. Preferred are compounds of formula I, wherein n is 1. Further preferred are compounds of formula I, wherein n is 2.

Also preferred are compounds of formula I, wherein n is 3.

Further preferred compounds are those compounds of formula I, wherein one of R⁶, R⁷ and R⁸ is

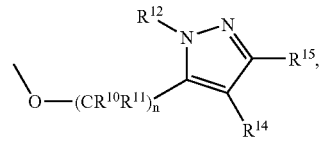

and R¹⁰ to R¹², R¹⁴, R¹⁵ and n are as defined herein before.
Especially preferred are those compounds, wherein R¹² is $C_{1-7}$-alkyl or fluoro-$C_{1-7}$-alkyl.

Also preferred are compounds of formula I, wherein one of R⁶, R⁷ and R⁸ is

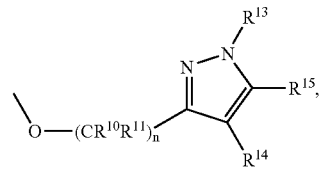

and R¹⁰, R¹¹, R¹³ to R¹⁵ and n are as defined herein before.

Compounds of formula I, wherein R¹⁵ is aryl, are preferred. More preferred are those compounds of formula I, wherein R¹⁵ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano, with those compounds, wherein R¹⁵ is phenyl substituted with halogen, fluoro-$C_{1-7}$-alkyl or fluoro-$C_{1-7}$-alkoxy, being particularly preferred.

Examples of preferred compounds of formula I are the following:
{6-[5-(4-trifluoromethyl-phenyl)-1H-pyrazol-3-yl-methoxy]-indol-1-yl}-acetic acid,
{6-[5-(4-chloro-phenyl)-2,4-dimethyl-2H-pyrazol-3-yl-methoxy]-indol-1-yl}-acetic acid,
{6-[2-methyl-5-(4-trifluoromethyl-phenyl)-2H-pyrazol-3-ylmethoxy]-indol-1-yl}-acetic acid,
{6-[5-(4-chloro-phenyl)-4-ethyl-2-methyl-2H-pyrazol-3-yl-methoxy]-indol-1-yl}-acetic acid,
{6-[5-(4-chloro-phenyl)-2-methyl-2H-pyrazol-3-yl-methoxy]-indol-1-yl}-acetic acid,
{5-[5-(4-chloro-phenyl)-1-methyl-1H-pyrazol-3-yl-methoxy]-indol-1-yl}-acetic acid,
{6-[2-ethyl-5-(4-trifluoromethyl-phenyl)-2H-pyrazol-3-yl-methoxy]-indol-1-yl}-acetic acid,
{6-[4-bromo-2-methyl-5-(4-trifluoromethyl-phenyl)-2H-pyrazol-3-ylmethoxy]-indol-1-yl}-acetic acid,
(5-{2-[2-methyl-5-(4-trifluoromethyl-phenyl)-2H-pyrazol-3-yl]-ethoxy}-indol-1-yl)-acetic acid,
{6-[2,4-dimethyl-5-(4-trifluoromethyl-phenyl)-2H-pyrazol-3-ylmethoxy]-indol-1-yl}-acetic acid, {6-[2-methyl-5-(4-trifluoromethoxy-phenyl)-2H-pyrazol-3-ylmethoxy]-indol-1-yl}-acetic acid,
{5-[2-methyl-5-(4-trifluoromethoxy-phenyl)-2H-pyrazol-3-ylmethoxy]-indol-1-yl}-acetic acid,
{6-[2-(2,2,2-trifluoro-ethyl)-5-(4-trifluoromethyl-phenyl)-2H-pyrazol-3-ylmethoxy]-indol-1-yl}-acetic acid,
{4-methyl-6-[2-methyl-5-(4-trifluoromethoxy-phenyl)-2H-pyrazol-3-ylmethoxy]-indol-1-yl}-acetic acid tert-butyl ester,
{6-[2-(2,2,2-trifluoro-ethyl)-5-(4-trifluoromethoxy-phenyl)-2H-pyrazol-3-ylmethoxy]-indol-1-yl}-acetic acid,
{6-[1-methyl-5-(4-trifluoromethoxy-phenyl)-1H-pyrazol-3-ylmethoxy]-indol-1-yl}-acetic acid,
{6-[5-(3,4-dichloro-phenyl)-2-methyl-2H-pyrazol-3-ylmethoxy]-indol-1-yl}-acetic acid,
{6-[5-(4-fluoro-3-trifluoromethyl-phenyl)-2-methyl-2H-pyrazol-3-ylmethoxy]-indol-1-yl}-acetic acid,
(6-{2-[2-methyl-5-(4-trifluoromethoxy-phenyl)-2H-pyrazol-3-yl]-ethoxy}-indol-1-yl)-acetic acid,
(6-{3-[2-methyl-5-(4-trifluoromethoxy-phenyl)-2H-pyrazol-3-yl]-propoxy}-indol-1-yl)-acetic acid,
(6-{2-[2-(2,2,2-trifluoro-ethyl)-5-(4-trifluoromethoxy-phenyl)-2H-pyrazol-3-yl]-ethoxy}-indol-1-yl)-acetic acid,
[rac]-2-{6-[2-(2,2,2-trifluoro-ethyl)-5-(4-trifluoromethoxy-phenyl)-2H-pyrazol-3-ylmethoxy]-indol-1-yl}-propionic acid,
{6-[2-difluoromethyl-5-(4-trifluoromethoxy-phenyl)-2H-pyrazol-3-ylmethoxy]-indol-1-yl}-acetic acid,
[rac]-2-{6-[2-methyl-5-(4-trifluoromethoxy-phenyl)-2H-pyrazol-3-ylmethoxy]-indol-1-yl}-propionic acid,
(6-{3-[2-methyl-5-(4-trifluoromethyl-phenyl)-2H-pyrazol-3-yl]-propoxy}-indol-1-yl)-acetic acid.

Particularly preferred compounds of formula I of the present invention are the following:
{6-[2-methyl-5-(4-trifluoromethyl-phenyl)-2H-pyrazol-3-ylmethoxy]-indol-1-yl}-acetic acid,
(5-{2-[2-methyl-5-(4-trifluoromethyl-phenyl)-2H-pyrazol-3-yl]-ethoxy}-indol-1-yl)-acetic acid,
{6-[2,4-dimethyl-5-(4-trifluoromethyl-phenyl)-2H-pyrazol-3-ylmethoxy]-indol-1-yl}-acetic acid,
{6-[2-methyl-5-(4-trifluoromethoxy-phenyl)-2H-pyrazol-3-ylmethoxy]-indol-1-yl}-acetic acid,
{6-[2-(2,2,2-trifluoro-ethyl)-5-(4-trifluoromethyl-phenyl)-2H-pyrazol-3-ylmethoxy]-indol-1-yl}-acetic acid,
(6-{2-[2-methyl-5-(4-trifluoromethoxy-phenyl)-2H-pyrazol-3-yl]-ethoxy}-indol-1-yl)-acetic acid,
(6-{3-[2-methyl-5-(4-trifluoromethoxy-phenyl)-2H-pyrazol-3-yl]-propoxy}-indol-1-yl)-acetic acid,
{6-[2-difluoromethyl-5-(4-trifluoromethoxy-phenyl)-2H-pyrazol-3-ylmethoxy]-indol-1-yl}-acetic acid,
(6-{3-[2-methyl-5-(4-trifluoromethyl-phenyl)-2H-pyrazol-3-yl]-propoxy}-indol-1-yl)-acetic acid.

Especially preferred are also the following compounds of formula I of the present invention:
{6-[2-methyl-5-(4-trifluoromethoxy-phenyl)-2H-pyrazol-3-ylmethoxy]-indol-1-yl}-acetic acid,
{6-[2-(2,2,2-trifluoro-ethyl)-5-(4-trifluoromethyl-phenyl)-2H-pyrazol-3-ylmethoxy]-indol-1-yl}-acetic acid,
(6-{3-[2-methyl-5-(4-trifluoromethoxy-phenyl)-2H-pyrazol-3-yl]-propoxy}-indol-1-yl)-acetic acid,
(6-{3-[2-methyl-5-(4-trifluoromethyl-phenyl)-2H-pyrazol-3-yl]-propoxy}-indol-1-yl)-acetic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula (I) as defined above, which process comprises reacting a compound of formula

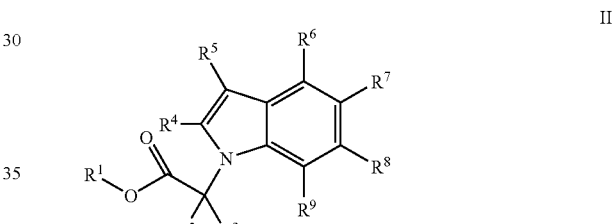

II wherein $R^1$ is $C_{1-7}$-alkyl, $R^2$, $R^3$, $R^4$ and $R^5$ are as defined as in claim 1 and $R^6$, $R^7$, $R^8$ and $R^9$ are selected from hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl, and cyano with the proviso that one of $R^6$, $R^7$ or $R^8$ is —OH, with a compound of formula

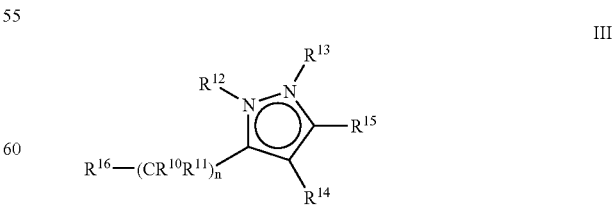

III wherein X, Y, $R^{10}$, $R^{11}$, $R^{12}$, $R^{13}$, $R^{14}$, $R^{15}$ and n are as defined in claim 1 and $R^{16}$ is —OH, —Cl, —Br, —I or another leaving group, to obtain a compound of formula

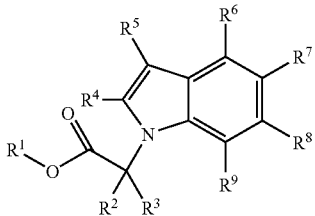

I wherein $R^1$ is $C_{1-7}$-alkyl and $R^2$ to $R^9$ are as defined in claim 1, and optionally hydrolysing the ester group to obtain a compound of formula I, wherein $R^1$ is or, alternatively, reacting a compound of formula

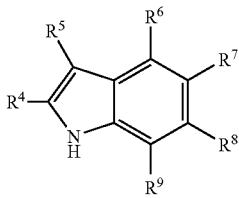

IV wherein $R^4$ to $R^9$ are as defined as in claim 1, with a compound of formula

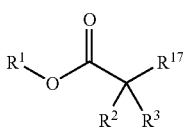

V wherein $R^1$ is $C_{1-7}$-alkyl, $R^2$ and $R^3$ are as defined in claim 1 and $R^{17}$ is halogen, triflate or another leaving group, to obtain a compound of formula

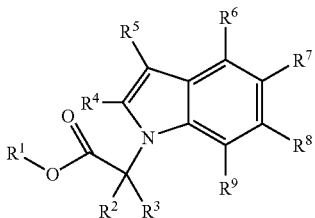

I wherein $R^1$ is $C_{1-7}$-alkyl and $R^2$ to $R^9$ are as defined in claim 1, and optionally hydrolysing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists.

Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Compounds of formula (I) (compounds 7 and 8 in scheme 1) can be synthesized according to the methods depicted in scheme 1 for $R^8$ being equal to

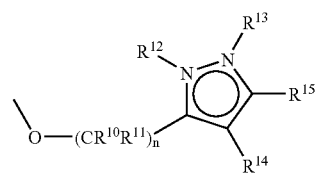

with $R^{10}$, $R^{11}$, $R^{12}$, $R^{13}$, $R^{14}$, $R^{15}$ and n having the meanings as defined herein before.

The same reaction sequences can be applied to synthesize compounds of formula (I) where $R^6$ or $R^7$ is equal to

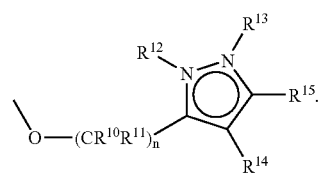

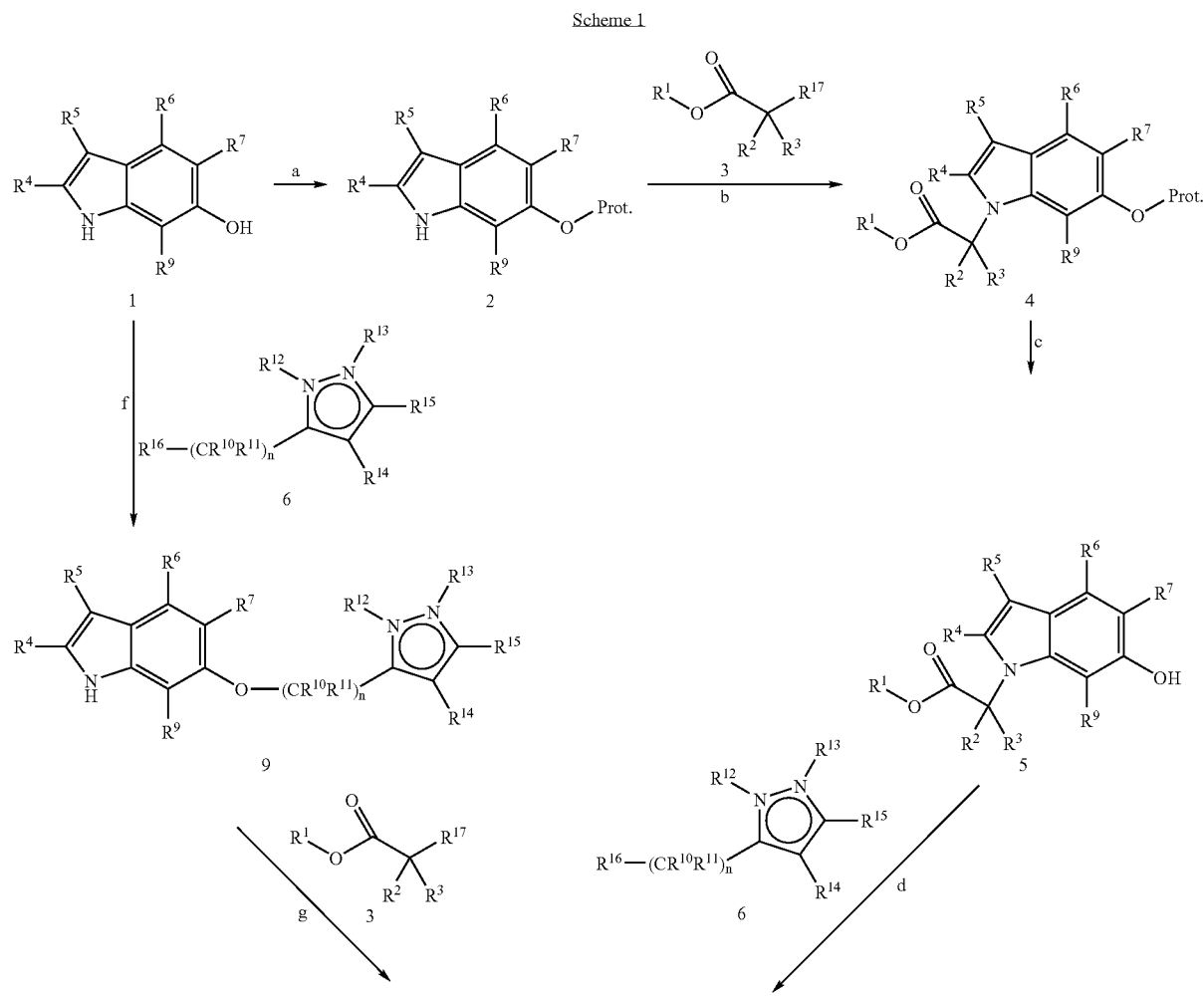

Scheme 1

-continued

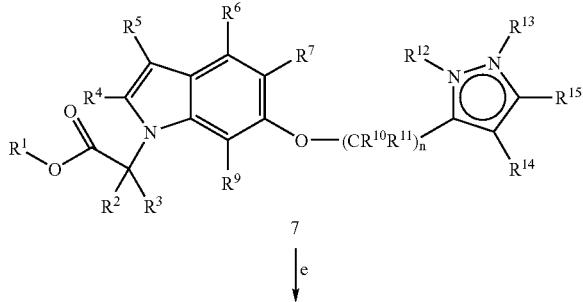

7

↓ e

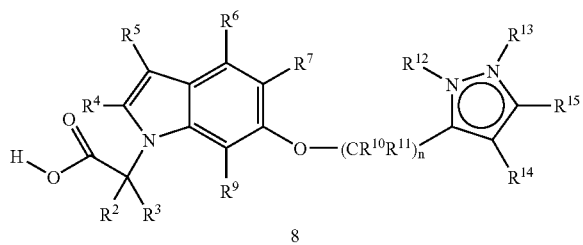

8

6-Hydroxyindols 1 and the regioisomeric 4- and 5-hydroxyindols are commercially available, known or can be synthesized by methods known in the art. The hydroxy function of compounds 1 can be protected by methods described in the literature, e.g. by treating them with tert-butyldimethylsilyl chloride in the presence of imidazole, preferably at room temperature in solvents like N,N-dimethylformamide, to obtain the corresponding tert-butyldimethylsilyl ethers 2 (step a). N-Alkylation of intermediates 2 with carboxylic acid ester 3, where $R^{17}$ can be equal to e.g. chlorine, bromine, triflate, or another leaving group, delivers indoles 4 and can be performed by standard technology; e.g. in the presence of $K_2CO_3$ or $Cs_2CO_3$ at temperatures between 10° C. and the reflux temperature of the solvent in a solvent like acetonitrile or acetone or in the presence of sodium hydride at temperatures between −10° C. and 50° C. in a solvent like N,N-dimethylformamide (step b). Ester derivatives 3 are commercially available or can be synthesized by methods known in the art. Deprotection of indoles 4 by methods described in the literature, e.g. by treatment with tetrabutyl ammonium fluoride at temperatures between −15° C. and ambient temperature in a solvent like tetrahydrofuran, provided that the protection group is a silyl ether, gives hydroxyindols 5 (step c). Pyrazole compounds 6 (prepared as outlined in schemes 3-6) are condensed with hydroxyindols 5 according to well known procedures: if $R^{16}$ represents a hydroxy group e.g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature. Alternatively, if $R^{16}$ represents a halide, mesylate or tosylate moiety, the pyrazole compounds 6 can be reacted with hydroxyindols 5 in solvents like N,N-dimethylformamide, acetonitrile, acetone or methyl-ethyl ketone in the presence of a weak base like cesium or potassium carbonate in a temperature ranging from room temperature to 140° C., preferably around 50° C., to yield ether compounds 7 (step d). Those can optionally be hydrolyzed according to standard procedures, e.g. by treatment with an alkali hydroxide like LiOH or NaOH in a polar solvent mixture like tetrahydrofuran/ethanol/water leading to carboxylic acids 8 (step e). If the pyrazole compounds 6 (prepared as described in schemes 3-6) and/or the hydroxyindols 5 contain chiral centers, ester compounds 7 and carboxylic acids 8 are obtained as mixtures of diastereomers or enantiomers, which can be separated by methods well known in the art, e.g. (chiral) HPLC or crystallization.

Carboxylic acid esters 7 can alternatively be synthesized via regioselective condensation of pyrazoles 6 with hydroxyindols 1 under the conditions given in step d (step f) and subsequent alkylation of the obtained ethers 9 with alkylating reagents 3 as described for the synthesis of esters 4 in step b (step g).

6-Hydroxyindoles 1 (scheme 1) and O-protected 6-hydroxyindols 2 (scheme 1) as well as their regioisomeric 4- and 5-hydroxyindol analogues are known or can be synthesized by methods known in the art. Examples for possible syntheses of these key intermediates (compounds 6 and 7 in scheme 2) are given in scheme 2 for $R^8$ in I being equal to hydroxy or protected hydroxy. Analogous key intermediates where $R^6$ or $R^7$ is equal to hydroxy or hydroxy carrying a protecting group can be synthesized applying the same reaction sequence.

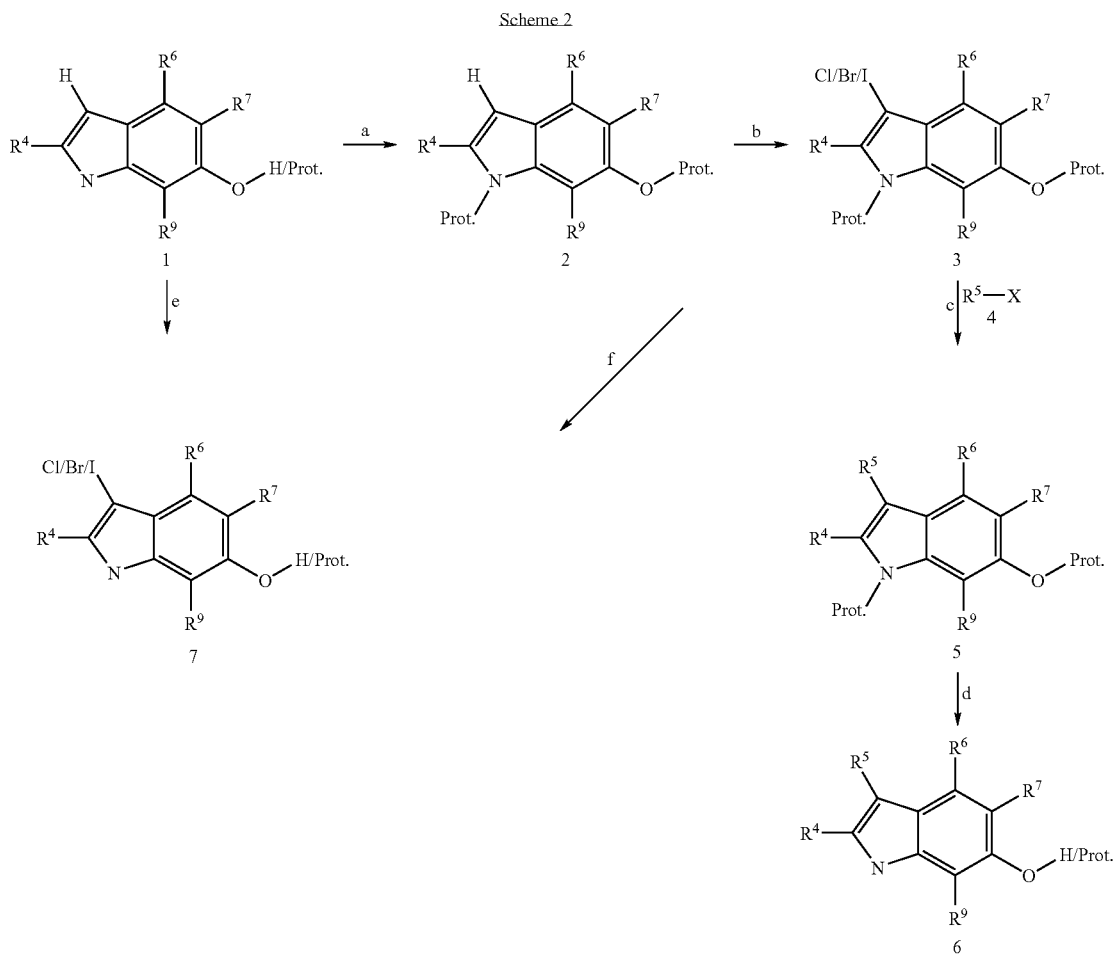

Scheme 2

Introduction of a protecting group at the nitrogen atom of indols 1 can be performed under standard conditions, e.g. by deprotonation with a base like n-butyllithium, preferably at −78° C., and subsequent addition of e.g. tert-butyldimethylsilyl chloride at temperatures between −78° C. and ambient temperature in solvents like tetrahydrofuran (step a). Halogenation of protected indols 2, e.g. through reaction with N-bromosuccinimide at temperatures between −78° C. and ambient temperature in solvents like tetrahydrofuran delivers 3-halo indols 3 (step b). Compounds 3 can—following halogen metal exchange, preferably with tert-butyllithium at −78° C. in solvents like tetrahydrofuran—be reacted with alkylating reagents 4 with X e.g. being a chlorine, bromine or iodine atom, preferably with alkyl iodides, at temperatures between −78° C. and ambient temperature in solvents like tetrahydrofuran, to form indols 5 bearing a substituent in position 3 (step c). N-Deprotection or simultaneous N- and O-deprotection of compounds 5 leading to building blocks 6 can be performed by methods described in the literature, e.g. by treatment with tetrabutyl ammonium fluoride at temperatures between −15° C. and ambient temperature in a solvent like tetrahydrofuran, if the protecting groups are silyl ethers and/or silylated indoles (step d).

Building blocks 7 carrying a chlorine, bromine or iodine substituent in position 3 can be synthesized by halogenation of indols 1, optionally carrying a protecting group at the hydroxy function, e.g. by reaction with N-chlorosuccinimide at temperatures between −15° C. and the reflux temperature of the solvent in solvents like dichloromethane or chloroform (step e). Alternatively, the same halo-indols 7 can be obtained via N-deprotection or N- and O-deprotection of indols 3 as described in step d (step f).

Pyrazoles 6 (scheme 1) are commercially available, known or can be synthesized by methods known in the art. Representative examples of possible syntheses of these key intermediates are given in schemes 3-6.

Scheme 3

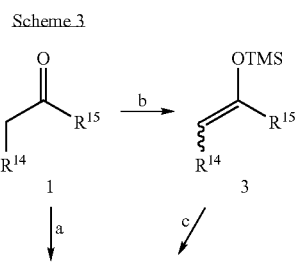

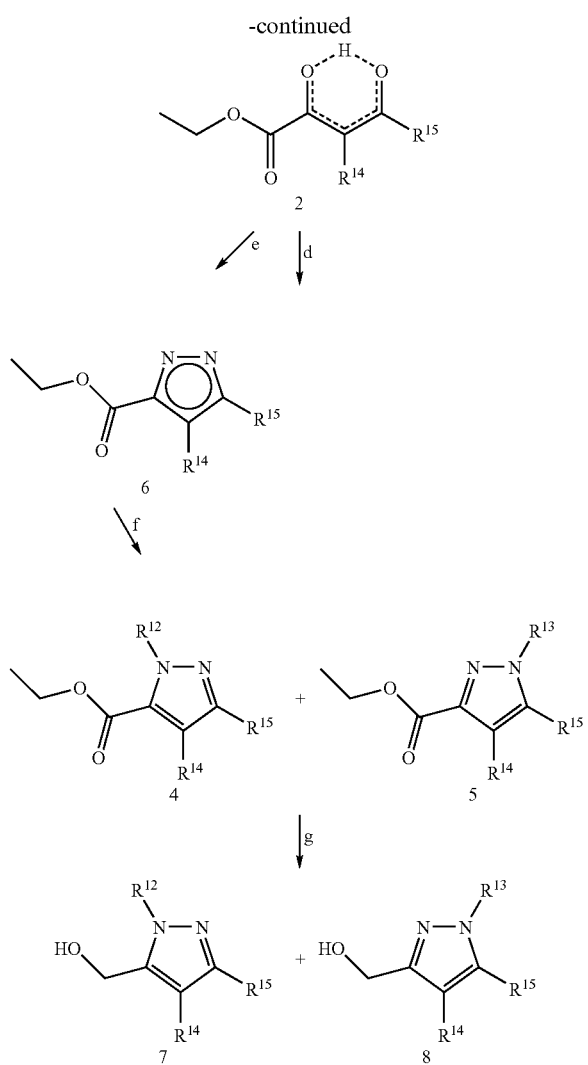

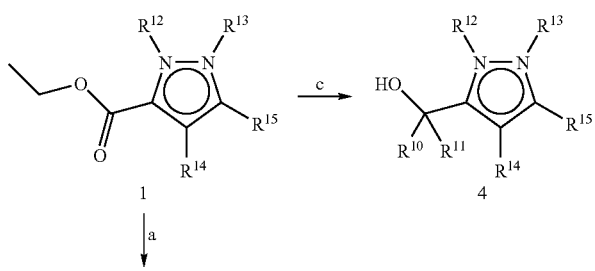

with diethyl oxalate in the presence of a base like sodium ethoxide at temperatures between −78° C. and 50° C. in solvents like ethanol, or with with lithium hexamethyldisilazide at temperatures between −78° C. and ambient temperature in solvents like ether, to form after subsequent acidification free ethyl pyruvates 2 (step a). Alternatively, pyruvates 2 can be synthesized via i) transforming ketones 1 into the corresponding silyl enol ethers 3, e.g. through treatment with trimethylsilyl chloride in the presence of a base like triethylamine at temperatures between 0° C. and 40° C. in a solvent like acetonitrile (step b); ii) in situ formation of a metal enol ether, e.g. with zinc chloride and subsequent acylation with an acylation reagent like ethyl oxalyl chloride at temperatures between 0° C. and 50° C. in a solvent like toluene or dichloromethane (step c). Pyruvates 2 can be converted to regioisomeric pyrazoles 4 and 5 through condensation with monosubstituted hydrazines H₂NNHR$^{12/13}$ which are commercially available, known or can be prepared by methods known in the art, e.g. at temperatures between ambient temperature and the reflux temperature of the solvent in solvents like ethanol (step d). Alternatively, pyrazoles 4 and 5 can be synthesized via i) reacting pyruvates 2 with hydrazine, preferably at reflux temperature in ethanol (step e); ii) conversion of the obtained pyrazole 6 into regioisomeres 4 and 5 under standard conditions, e.g. through alkylation with an alkyl halogenide in the presence of a base like potassium hydroxide at temperatures between −78° C. and the reflux temperature of the solvent in solvents like ethanol (step f). Regioisomeric pyrazoles 4 and 5 can easily be separated by techniques well known in the art, e.g. through column chromatography on silica. Reduction of esters 4 and 5 can be performed by methods well known in the art, e.g. with lithium aluminium hydride at temperatures between 0° C. and the reflux temperature of the solvents in solvents like tetrahydrofuran or diethyl ether (step g).

The alcohol compounds 7 and 8 correspond to or can be converted into compounds of general formula 6 (scheme 1), e.g. by treatment with methanesulfonyl chloride in dichloromethane in the presence of a base like triethylamine preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

Substituted acetophenones and heteroaryl ketones 1 are commercially available, known or can be prepared by methods known in the art. Acylation of compounds 1 with oxalate derivatives can be performed under standard conditions, e.g.

-continued

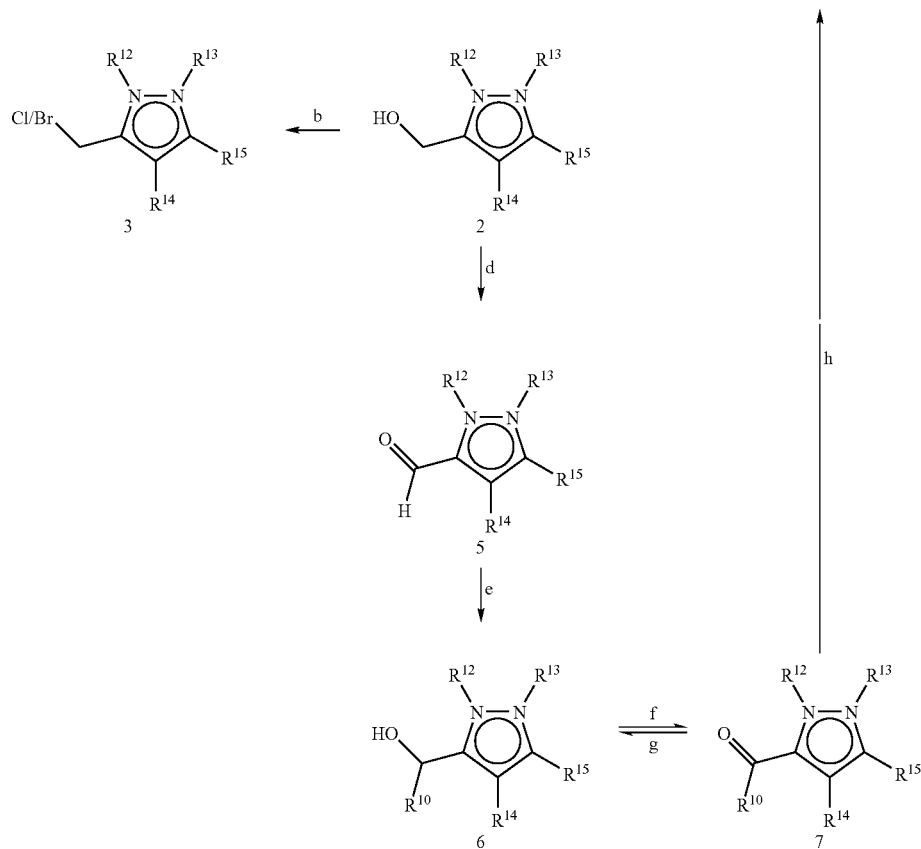

Reduction of pyrazole esters 1 (compounds 4, 5 and 6 in scheme 3), preferably using lithium aluminum hydride in a solvent like ether or tetrahydrofuran, preferably between 0° C. and room temperature, gives primary alcohols 2 (step a), which can be used as such or can be converted into the corresponding halides 3, e.g. by treatment with methanesulfonyl chloride in dichloromethane in the presence of 2,6-lutidine, preferably between −20° C. and the reflux temperature of dichloromethane, by treatment with thionyl chloride in a solvent like dichloromethane or chloroform, preferably at temperatures between −20° C. and +50° C., or by treatment with tetrabromomethane and triphenylphosphine in solvents like tetrahydrofuran at temperatures between 0° C. and the reflux temperature of tetrahydrofuran (step b). Esters 1 can further be converted into tertiary alcohols 4 with $R^{10}=R^{11}$ through reaction with alkyl organometallic reagents, preferably using alkyl Grignard compounds in a solvent like tetrahydrofuran or ether, preferably between −15° C. and the reflux temperature of the solvent (step c). Alcohols 4 with $R^{10}$ not equal to $R^{11}$ can be prepared by a sequential procedure: i) saponification to the acid; ii) treatment with $R^{10}Li$, optionally in the presence of a Cu(I) salt, in ether or tetrahydrofuran to yield the alkyl ketones —$COR^{10}$; iii) subsequent reaction with $R^{11}Li$ or lithium aluminium hydride in ether or tetrahydrofuran (step c). Primary alcohols 2 can be oxidized to aldehydes 5 by methods known in the art, e.g. by treatment with pyridinium chlorochromate in dichloromethane, preferably at temperatures between room temperature and the reflux temperature of dichloromethane, or by treatment with manganese dioxide in solvents like dichloromethane, preferably at room temperature (step d). These aldehydes 5 can be converted to the corresponding secondary alcohols 6 through reaction with alkyl organometallic compounds, preferably under the conditions given for the transformation of esters 1 to tertiary alcohols 4 (step e). Ketones 7 can be obtained from secondary alcohols 6 by methods known in the art, e.g. by treatment with Cr(VI) reagents like the Jones reagent (Jones et al., J. Chem. Soc. 1953, 2548.) (step f). These ketones 7 can be reduced back to the corresponding secondary alcohols 6 in an enantioselective fashion leading to the (R)- or (S)-alcohols 6, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, J. Am. Chem. Soc. 1987, 109, 5551-5553), or by treatment with (+)- or (−)-B-chlorodiisopinocampheylborane (DIP-Cl), according to Brown et al. (P. V. Ramachandran, B. Gong, A. V. Teodorovic, H. C. Brown, Tetrahedron: Asymmetry 1994, 5, 1061-1074) (step g). Ketones 7 can in addition be converted to the corresponding tertiary alcohols 4 through reaction with alkyl organometallic compounds, preferably under the conditions given for the transformation of esters 1 to tertiary alcohols 4 in step c (step h). If the alcohol compounds 2, 4, or 6 contain one or more chiral centers and are not optically pure, they can optionally be separated into optically pure antipodes by methods well known in the art, e.g. chromatography on a chiral HPLC column, or by derivatization with an optically pure acid to form esters, which can then be separated by conventional HPLC chromatography and converted back to the original alcohol.

The alcohols compounds 2, 4, and 6, and the halide compound 3, correspond to or can be converted into compounds of general formula 6 (scheme 1), e.g. by treatment with methanesulfonyl chloride in dichloromethane in the presence of a base like triethylamine preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

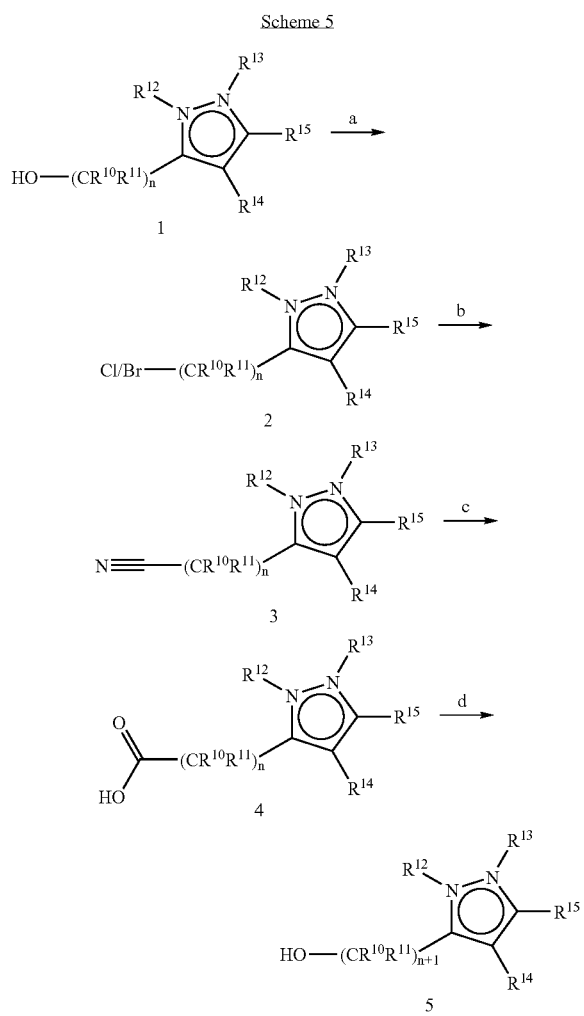

Pyrazole alkanols 1 with a chain length of n carbon atoms can be converted into analogues with a chain length of n+1 carbon atoms by methods well known in the art, e.g. by conversion of the primary alcohol function into a suitable leaving group, e.g. a halide (step a), reaction with cyanide ion (step b), saponification (step c) followed by reduction of the acid formed (compounds 4) to the primary alcohols 5, e.g. by using diborane in tetrahydrofuran (step d). In order to introduce substituents $R^{10}$ and/or $R^{11}$ different from hydrogen, cyano intermediates 3 of this elongation process can be reacted with alkyl Grignard reagents $R^{10}$MgX in solvents like ether or tetrahydrofuran between 0° C. and the reflux temperature of the solvent to form the corresponding $R^{10}$CO-alkyl ketones, which upon treatment with an alkyllithium reagent $R^{11}$Li or lithium aluminum hydride in solvents like ether or tetrahydrofuran give alcohols 5. $R^{10}$CO-alkyl ketones can also be reduced, e.g. by treatment with sodium borohydride in alcohol, preferably at temperatures between −15° C. and 40° C. This reaction can also be carried out in an enantioselective fashion leading to the (R)- or (S)-alcohols 5, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheylborane (DIP-Cl), according to Brown et al. (P. V. Ramachandran, B. Gong, A. V. Teodorovic, H. C. Brown, *Tetrahedron: Asymmetry* 1994, 5, 1061-1074). Alternatively, alcohol compounds 5 which contain one or more chiral centers can optionally be separated into optically pure antipodes by methods well known in the art, e.g. chromatography on a chiral HPLC column, or by derivatization with an optically pure acid to form esters, which can then be separated by conventional HPLC and converted back to the original alcohol. The alcohol compounds 5 correspond to or can be transformed into compounds of general formula 6 (scheme 1), e.g. by treatment with methanesulfonyl chloride in dichloromethane in the presence of a base like triethylamine, preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

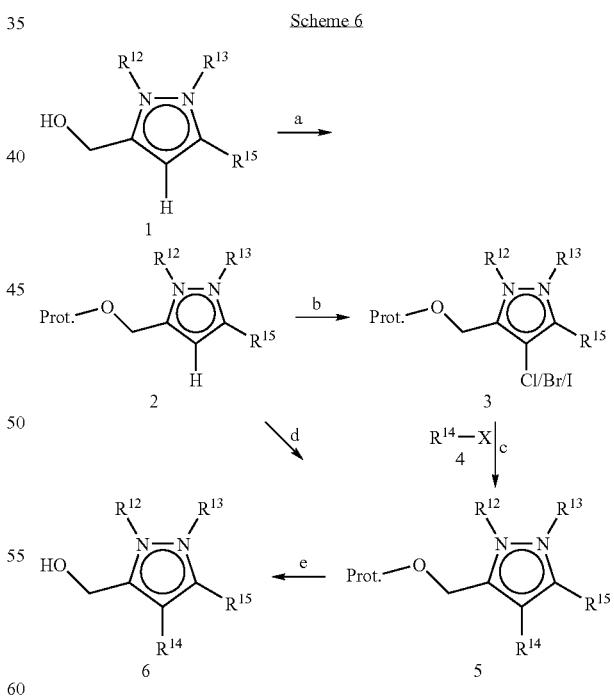

Alcohols 1 (compounds 6 with $R^{14}$=H and $R^{6}$=OH in scheme 1, compounds 7 and 8 with $R^{14}$=H in scheme 3, compounds 2, 4 and 6 with $R^{14}$=H in scheme 4, compounds 1 and 5 with $R^{14}$=H in scheme 5) can be protected by methods known in the literature, e.g. by treating them with tert-butyldimethylsilyl chloride in the presence of imidazole, preferably at room temperature in solvents like N,N-dimethylformamide, to obtain the corresponding tert-butyldimethylsilyl ethers 2 (step a). Halogenation of protected pyrazoles 2, e.g. through reaction with bromine preferably at temperatures between 0° C. and ambient temperature in solvents like dichloromethane delivers 4-halo pyrazoles 3 (step b). Compounds 3 can—following halogen metal exchange, preferably with tert-butyllithium at −78° C. in solvents like tetrahydrofuran—be reacted with alkylating reagents 4 with X e.g. being a chlorine, bromine or iodine atom, preferably with alkyl iodides, at temperatures between −78° C. and ambient temperature in solvents like tetrahydrofuran, to form pyrazoles 5 bearing a substituent in position 4 (step c). Alternatively, transition metal catalyzed reactions can be used to transform 4-halo pyrazoles 3 into compounds 5, e.g. by treatment with a stannane (X being trialkyl stannyl) in the presence of a Pd(0) catalyst like [Pd$_2$(dba)$_3$] and triphenyl arsine at temperatures between 0° C. and the reflux temperature of the solvent in solvents like dioxane. Residues $R^{14}$ can further be introduced by i) formylation of pyrazoles 2 through methods well known in the art, e.g. with phosphorus oxychloride and N,N-dimethylformamide preferably at temperatures between 0° C. and 100° C.; ii) subsequent transformation of the intermediate formyl pyrazole to 4-substituted pyrazoles 5, e.g. through reduction with sodium cyano borohydride in the presence of zinc iodide at temperatures between −78° C. and the reflux temperature of the solvent in solvents like diethyl ether (step d). O-Deprotection of compounds 5 leading to building blocks 6 can be performed by methods described in the literature, e.g. by treatment with tetrabutyl ammonium fluoride at temperatures between −15° C. and ambient temperature in a solvent like tetrahydrofuran, if the protecting groups are silyl ethers (step e). The alcohol compounds 6 correspond to or can be transformed into compounds of general formula 6 (scheme 1), e.g. by treatment with methanesulfonyl chloride in dichloromethane in the presence of a base like triethylamine, preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112-119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM MgCl$_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resuspended in 50 μl of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 μl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 μg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containig the recptor-coated beads was resolved in 50 μl of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 μl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was was discarded and then 50 μl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.1 nM to 10 μM, preferably 1 nM to 500 nM for PPARδ and/or $IC_{50}$ values of 1 nM to 10 μM, preferably 10 nM to 5 μM for PPARα. Compounds, in which $R^1$ is not hydrogen are converted in vivo to compounds in which $R^1$ is hydrogen. The following table 1 shows measured values for some selected compounds of the present invention.

TABLE 1

| | PPARα $IC_{50}$ (μmol/l) | PPARγ $IC_{50}$ (μmol/l) | PPARδ $IC_{50}$ (μmol/l) |
|---|---|---|---|
| Example 2 | 10 | 10 | 0.140 |
| Example 8 | 2.57 | 10 | 0.004 |
| Example 20 | 0.013 | 10 | 0.043 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Abbreviations:

AcOEt=ethyl acetate, DMF=N,N-dimethylformamide, DMPU=1,3-dimethyl-3,4,5,6-tetrahydro-2(1H)-pyrimidinone, LDA=lithium diisopropylamide, MeOH=methanol, quant.=quantitative, RT=room temperature, THF=tetrahydrofuran.

Example 1 a] [5-(4-Trifluoromethyl-phenyl)-1H-pyrazol-3-yl]-methanol

A solution of 5-(4-trifluoromethyl-phenyl)-1H-pyrazole-3-carboxylic acid ethyl ester (160 mg, 0.56 mmol; PCT Int. Appl. (2003), WO 2004000785 A2) in tetrahydrofuran (2.5 ml) was added to a suspension of lithium aluminium hydride (43 mg, 1.13 mmol) in tetrahydrofuran (2.5 ml) under an argon atmosphere at ambient temperature within 5 min. The mixture was heated to reflux for 12 h, cooled to 0° C. and treated cautiously with water (2 ml) and 10% aqueous NaOH (0.5 ml). The reaction mixture was filtered over celite, ice water/ethyl acetate 1/1 was added and the layers were separated. The aqueous layer was extracted one more time with ethyl acetate, the combined organic layers were washed with ice water/brine 1/1 and dried over sodium sulfate. Removal of the solvent under reduced pressure gave 81 mg (0.33 mmol, 59%) of the title compound as white solid.

MS: 243.1 $(M+H)^+$.

b] 3-Chloromethyl-5-(4-trifluoromethyl-phenyl)-1H-pyrazole

To a solution of [5-(4-trifluoromethyl-phenyl)-1H-pyrazol-3-yl]-methanol (40 mg, 0.17 mmol) in chloroform (4 ml) was added thionyl chloride (0.34 ml, 4.7 mmol) at 0° C. under an argon atmosphere. The solution was stirred at 40° C. for 2 h and at 60° C. for 10 min. The mixture was poured onto ice water/aqueous NaHCO$_3$ 1/1, extracted two times with dichloromethane and the combinded extracts were dried over sodium sulfate. Evaporation of the solvent under reduced pressure gave 43 mg (0.165 mmol, 97%) of the title compound as white crystals.

c] [6-(tert-Butyl-dimethyl-silanyloxy)-indol-1-yl]-acetic acid tert-butyl ester To an ice cold solution of 6-(tert-butyl-dimethyl-silanyloxy)-1H-indole (13 g, 52.5 mmol) and cesium carbonate (18.8 g, 57.8 mmol) in DMF (130 ml) under an argon atmosphere was added bromo-acetic acid tert-butyl ester (8.5 ml, 57.8 mmol). The mixture was naturally warmed to room temperature, stirred for 14 h, poured onto 2 N HCl/ice water 1/1 and extracted two times with ethyl acetate. The combined organic layers were washed with water and dried over sodium sulfate. The solvent was removed under reduced pressure and the residue purified by column chromatography (silica gel, heptane/AcOEt) to give 14.3 g (39.6 mmol, 75%) of the title compound as yellow oil.

MS: 362.4 (M+H)$^+$.

d] (6-Hydroxy-indol-1-yl)-acetic acid tert-butyl ester

To an ice cooled solution of [6-(tert-butyl-dimethyl-silanyloxy)-indol-1-yl]-acetic acid tert-butyl ester (4.2 g, 11.6 mmol) in THF (24 ml) was added a 1 M solution of tetrabutylammonium fluoride in THF (11.6 ml, 11.6 mmol) within 15 min. The reaction mixture was stirred for 1 h at ambient temperature, poured onto 1 N HCl/ice water 1/1 and extracted two times with ethyl acetate. The combined organic layers were washed with brine/ice water 1/1 and dried over sodium sulfate. The solvent was removed under reduced pressure to give 3.4 g (quant.) of the title compound as brown oil which was used in the next step without further purification.

MS: 265.5 (M+NH$_4$)$^+$, 248.4 (M+H)$^+$.

e] [6-[5-(4-Trifluoromethyl-phenyl)-1H-pyrazol-3-ylmethoxy]-indol-1-yl]-acetic acid tert-butyl ester A mixture of (6-hydroxy-indol-1-yl)-acetic acid tert-butyl ester (37 mg, 0.15 mmol), 3-chloromethyl-5-(4-trifluoromethyl-phenyl)-1H-pyrazole (43 mg, 0.16 mmol), cesium carbonate (54 mg, 0.16 mmol) and a trace of potassium iodide were suspended in N,N-dimethylformamide (4 ml). The suspension was stirred at ambient temperature for 14 h and for 4 h at 80° C. The solvent was evaporated under reduced pressure and the residue dissolved in 1 N HCl/ice water 1/1 and ethyl acetate. The layers were separated and the aqueous layer was extracted two times with ethyl acetate. The combined organic layers were washed two times with brine and dried over sodium sulfate. The solvent was removed under reduced pressure and the residue purified by column chromatography (silica gel, heptane/AcOEt) to give 5 mg (10 μmol, 7%) of the title compound as orange oil.

f] {6-[5-(4-Trifluoromethyl-phenyl)-1H-pyrazol-3-ylmethoxy]-indol-1-yl}-acetic acid To a solution of {6-[5-(4-trifluoromethyl-phenyl)-1H-pyrazol-3-ylmethoxy]-indol-1-yl}-acetic acid tert-butyl ester (5 mg, 10 μmol) in THF/methanol 2/1 (750 μl) was added 1 N aqueous LiOH solution (600 μl). The reaction mixture was stirred for 14 h at ambient temperature and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (3 mg, 7 μmol, 68%) as brown crystals.

MS: 412.2 (M−H)$^−$.

Example 2 a] 5-(4-Chloro-phenyl)-2,4-dimethyl-2H-pyrazole-3-carboxylic acid ethyl ester and 5-(4-chloro-phenyl)-1,4-dimethyl-1H-pyrazole-3-carboxylic acid ethyl ester 5-(4-Chloro-phenyl)-4-methyl-1H-pyrazole-3-carboxylic acid ethyl ester (58 mg, 0.22 mmol; PCT Int. Appl. (1997), WO 9721682 A1) was added to a solution of KOH (15 mg, 0.27 mmol) in absolute ethanol (1.6 ml). The solution was stirred at ambient temperature for 15 min. Methyl iodide (30 μl, 0.44 mmol) was added and the reaction solution was heated under reflux for 2 h. The solvent was removed under reduced pressure and the residue dissolved in brine/ice water 1/1 and ethyl acetate. The layers were separated and the aqueous layer was extracted two times with ethyl acetate. The combined organic layers were washed with brine and dried over sodium sulfate. The solvent was removed under reduced pressure and the residue purified by column chromatography (silica gel, heptane/AcOEt) to give 29 mg (0.1 mmol, 47%) 5-(4-chloro-phenyl)-2,4-dimethyl-2H-pyrazole-3-carboxylic acid ethyl ester as colorless crystals and 22 mg (0.08 mmol, 36%) 5-(4-chloro-phenyl)-1,4-dimethyl-1H-pyrazole-3-carboxylic acid ethyl ester as colorless crystals.

5-(4-chloro-phenyl)-2,4-dimethyl-2H-pyrazole-3-carboxylic acid ethyl ester: MS: 279.0 (M+H)$^+$.
5-(4-chloro-phenyl)-1,4-dimethyl-1H-pyrazole-3-carboxylic acid ethyl ester: MS: 279.0 (M+H)$^+$.

b] [5-(4-Chloro-phenyl)-2,4-dimethyl-2H-pyrazol-3-yl]-methanol

In analogy to the procedure described for example 1 a], 5-(4-chloro-phenyl)-2,4-dimethyl-2H-pyrazole-3-carboxylic acid ethyl ester was reduced with lithium aluminium hydride to give [5-(4-chloro-phenyl)-2,4-dimethyl-2H-pyrazol-3-yl]-methanol as colorless crystals.

MS: 236.9 (M+H)$^+$.

c] 5-Chloromethyl-3-(4-chloro-phenyl)-1,4-dimethyl-1H-pyrazole

In analogy to the procedure described for example 1 b], [5-(4-chloro-phenyl)-2,4-dimethyl-2H-pyrazol-3-yl]-methanol was reacted with thionyl chloride for 20 min at 0° C. to give 5-chloromethyl-3-(4-chloro-phenyl)-1,4-dimethyl-1H-pyrazole as yellow oil.

MS: 255.1 (M+H)$^+$.

d] [6-(tert-Butyl-dimethyl-silanyloxy)-indol-1-yl]-acetic acid ethyl ester

To an ice cold solution of 6-(tert-butyl-dimethyl-silanyloxy)-1H-indole (1 g, 4.04 mmol) and cesium carbonate (1.45 g, 4.45 mmol) in DMF (10 ml) under an argon atmosphere was added bromo-acetic acid ethyl ester (490 μl, 4.45 mmol). The mixture was naturally warmed to room temperature, stirred for 14 h, poured onto 1 N HCl/ice water 1/1 and extracted two times with ethyl acetate. The combined organic layers were washed with water and dried over sodium sulfate. The solvent was removed under reduced pressure and the residue purified by column chromatography (silica gel, heptane/AcOEt) to give 1.2 g (3.6 mmol, 89%) of the title compound as yellow oil.

MS: 334.3 (M+H)$^+$.

e] (6-Hydroxy-indol-1-yl)-acetic acid ethyl ester

To an ice cold solution of [6-(tert-butyl-dimethyl-silanyloxy)-indol-1-yl]-acetic acid ethyl ester (1.15 g, 3.45 mmol) in THF (11.5 ml) was added a 1 M solution of tetrabutylammonium fluoride in THF (3.45 ml, 3.45 mmol) within 15 min. The reaction mixture was stirred for 1 h at ambient temperature, poured onto 1 N HCl/ice water 1/1 and extracted two times with ethyl acetate. The combined organic layers were washed with brine/ice water 1/1 and dried over sodium sulfate. The solvent was removed under reduced pressure and the residue purified by column chromatography (silica gel, heptane/AcOEt) to give 590 mg (2.7 mmol, 78%) of the title compound as colorless crystals.

MS: 219.0 (M)$^+$, 146.0.

f] {6-[5-(4-Chloro-phenyl)-2,4-dimethyl-2H-pyrazol-3-ylmethoxy]-indol-1-yl}-acetic acid ethyl ester In analogy to the procedure described for example 1 e], (6-hydroxy-indol-1-yl)-acetic acid ethyl ester was reacted with 5-chloromethyl-3-(4-chloro-phenyl)-1,4-dimethyl-1H-pyrazole in the presence of cesium carbonate and potassium iodide in acetone to give {6-[5-(4-chloro-phenyl)-2,4-dimethyl-2H-pyrazol-3-ylmethoxy]-indol-1-yl}-acetic acid ethyl ester as yellow crystals.

MS: 438.1 (M+H)$^+$.

g] {6-[5-(4-Chloro-phenyl)-2,4-dimethyl-2H-pyrazol-3-ylmethoxy]-indol-1-yl}-acetic acid In analogy to the procedure described for example 1 f], {6-[5-(4-chloro-phenyl)-2,4-dimethyl-2H-pyrazol-3-ylmethoxy]-indol-1-yl}-acetic acid ethyl ester was treated with LiOH to obtain {6-[5-(4-chloro-phenyl)-2,4-dimethyl-2H-pyrazol-3-ylmethoxy]-indol-1-yl}-acetic acid as colorless crystals.

MS: 410.3 (M+H)$^+$.

Example 3 a] 2-Methyl-5-(4-trifluoromethyl-phenyl)-2H-pyrazole-3-carboxylic acid ethyl ester and 1-methyl-5-(4-trifluoromethyl-phenyl)-1H-pyrazole-3-carboxylic acid ethyl ester In analogy to the procedure described for example 2 a], 5-(4-trifluoromethyl-phenyl)-1H-pyrazole-3-carboxylic acid ethyl ester (PCT Int. Appl. (2003), WO 2004000785 A2) was reacted with methyl iodide in the presence of potassium hydroxide to give 2-methyl-5-(4-trifluoromethyl-phenyl)-2H-pyrazole-3-carboxylic acid ethyl ester and 1-methyl-5-(4-trifluoromethyl-phenyl)-1H-pyrazole-3-carboxylic acid ethyl ester, both as colorless crystals.

2-methyl-5-(4-trifluoromethyl-phenyl)-2H-pyrazole-3-carboxylic acid ethyl ester: MS: 299.2 (M+H)$^+$.

methyl-5-(4-trifluoromethyl-phenyl)-2H-pyrazole-3-carboxylic acid ethyl ester: MS: 299.2 (M+H)$^+$.

b] [2-Methyl-5-(4-trifluoromethyl-phenyl)-2H-pyrazol-3-yl]-methanol

In analogy to the procedure described for example 1 a], 2-methyl-5-(4-trifluoromethyl-phenyl)-2H-pyrazole-3-carboxylic acid ethyl ester was reduced with lithium aluminium hydride to give [2-methyl-5-(4-trifluoromethyl-phenyl)-2H-pyrazol-3-yl]-methanol as white crystals.

MS: 243.1 (M+H)$^+$.

c] {6-[2-Methyl-5-(4-trifluoromethyl-phenyl)-2H-pyrazol-3-ylmethoxy]-indol-1-yl}-acetic acid ethyl ester To an ice cold solution of (6-hydroxy-indol-1-yl)-acetic acid ethyl ester (35 mg, 160 μmol; example 2 e]), [2-methyl-5-(4-trifluoromethyl-phenyl)-2H-pyrazol-3-yl]-methanol (41 mg, 160 μmol) and tributylphosphine (50 μl, 19 μmol) in tetrahydrofuran (3.5 ml) was added N,N,N',N'-tetramethyl azodicarboxamide (33 mg, 19 μmol). The cooling bath was removed and stirring continued for 14 h. The mixture was filtered over celite and the solvent removed under reduced pressure to give a brown oil which was purified by column chromatography (silica gel, heptane/AcOEt) to obtain 22 mg (50 μmol, 30%) of the title compound as colorless oil.

MS: 458.3 (M+H)$^+$.

d] {6-[2-Methyl-5-(4-trifluoromethyl-phenyl)-2H-pyrazol-3-ylmethoxy]-indol-1-yl}-acetic acid In analogy to the procedure described for example 1 f], {6-[2-methyl-5-(4-trifluoromethyl-phenyl)-2H-pyrazol-3-ylmethoxy]-indol-1-yl}-acetic acid ethyl ester was treated with LiOH to obtain {6-[2-methyl-5-(4-trifluoromethyl-phenyl)-2H-pyrazol-3-ylmethoxy]-indol-1-yl}-acetic acid as brown crystals.

MS: 428.5 (M–H)$^-$

Example 4 a] 3-(4-Chloro-benzoyl)-2-oxo-pentanoic acid ethyl ester

Under anhydrous conditions, a solution of potassium t-butoxide (292 mg, 2.6 mmol) in diethyl ether (100 ml) was cooled to –78° C. and stirred for 10 min under an argon atmosphere. Commercial 2 M LDA in heptane/THF/ethyl benzene (13 ml, 26 mmol) was added by syringe and the mixture stirred for 15 min. 4-Chlorobutyrophenone (5 g, 26 mmol) in diethyl ether (35 ml) was added dropwise over 30 min with stirring. After a further 30 min, diethyl oxalate (3.53 ml, 26 mmol) was added in one portion. The cooling bath was removed and the reaction stirred for 2.5 h after reaching ambient temperature. After standing 3 days, the precipitated brown solid was filtered. The solid was partitioned between 1 M HCl and ethyl acetate. The aqueous layer was extracted two times with ethyl acetate, the combined extracts were washed with brine and dried over sodium sulfate. Evaporation of the solid gave 740 mg (4.6 mmol, 18%) of the title compound as orange oil.

b] 5-(4-Chloro-phenyl)-4-ethyl-1H-pyrazole-3-carboxylic acid ethyl ester

Hydrazine monohydrate (0.13 ml, 3 mmol) was added at ambient temperature to a solution of 3-(4-chloro-benzoyl)-2-oxo-pentanoic acid ethyl ester (740 mg, 3 mmol) in ethanol (4 ml) under an argon atmosphere. The solution was stirred for 8 h at reflux temperature, the solvent was removed under reduced pressure and the residue partitioned between 1 M HCl/ice water and ethyl acetate. The aqueous layer was extracted two times with ethyl acetate, the combined extracts were washed with brine (3 times) and dried over sodium sulfate. Removal of the solvent under reduced pressure left an orange oil which was purified by column chromatography (silica gel, heptane/AcOEt) to give 355 mg (1.27 mmol, 49%) of the title compound as yellow crystals.

MS: 278.1 $(M+H)^+$.

c] 5-(4-Chloro-phenyl)-4-ethyl-2-methyl-2H-pyrazole-3-carboxylic acid ethyl ester and 5-(4-chloro-phenyl)-4-ethyl-1-methyl-1H-pyrazole-3-carboxylic acid ethyl ester In analogy to the procedure described for example 2 a], 5-(4-chloro-phenyl)-4-ethyl-1H-pyrazole-3-carboxylic acid ethyl ester was reacted with methyl iodide in the presence of potassium hydroxide to to give 5-(4-chloro-phenyl)-4-ethyl-2-methyl-2H-pyrazole-3-carboxylic acid ethyl ester as yellow crystals and 5-(4-chloro-phenyl)-4-ethyl-1-methyl-1H-pyrazole-3-carboxylic acid ethyl ester as yellow oil.

5-(4-chloro-phenyl)-4-ethyl-2-methyl-2H-pyrazole-3-carboxylic acid ethyl ester: MS: 293.0 $(M+H)^+$.

5-(4-chloro-phenyl)-4-ethyl-1-methyl-1H-pyrazole-3-carboxylic acid ethyl ester: MS: 332.3 $(M+K)^+$.

d] [5-(4-Chloro-phenyl)-4-ethyl-2-methyl-2H-pyrazol-3-yl]-methanol

In analogy to the procedure described for example 1 a], 5-(4-chloro-phenyl)-4-ethyl-2-methyl-2H-pyrazole-3-carboxylic acid ethyl ester was reduced with lithium aluminium hydride to give [5-(4-chloro-phenyl)-4-ethyl-2-methyl-2H-pyrazol-3-yl]-methanol as colorless crystals.

MS: 251.0 $(M+H)^+$.

e] {6-[5-(4-Chloro-phenyl)-4-ethyl-2-methyl-2H-pyrazol-3-ylmethoxy]-indol-1-yl}-acetic acid tert-butyl ester In analogy to the procedure described for example 3 c], (6-hydroxy-indol-1-yl)-acetic acid tert-butyl ester (example 1 d]) was reacted with [5-(4-chloro-phenyl)-4-ethyl-2-methyl-2H-pyrazol-3-yl]-methanol in the presence of N,N,N',N'-tetramethyl azodicarboxamide and tributylphosphine to give {6-[5-(4-chloro-phenyl)-4-ethyl-2-methyl-2H-pyrazol-3-ylmethoxy]-indol-1'-yl}-acetic acid tert-butyl ester as colorless oil.

MS: 480.3 $(M+H)^+$.

f] {6-[5-(4-Chloro-phenyl)-4-ethyl-2-methyl-2H-pyrazol-3-ylmethoxy]-indol-1-yl}-acetic acid In analogy to the procedure described for example 1 f], {6-[5-(4-chloro-phenyl)-4-ethyl-2-methyl-2H-pyrazol-3-ylmethoxy]-indol-1-yl}-acetic acid tert-butyl ester was treated with LiOH to obtain {6-[5-(4-chloro-phenyl)-4-ethyl-2-methyl-2H-pyrazol-3-ylmethoxy]-indol-1-yl}-acetic acid as brown crystals.

MS: 422.1 $(M-H)^-$.

Example 5 a] 5-(4-Chloro-phenyl)-2-methyl-2H-pyrazole-3-carboxylic acid ethyl ester and 5-(4-chloro-phenyl)-1-methyl-1H-pyrazole-3-carboxylic acid ethyl ester In analogy to the procedure described for example 2 a], 5-(4-chloro-phenyl)-1H-pyrazole-3-carboxylic acid ethyl ester (T. van Herk et al., *J. Med. Chem.* 2003, 46, 3945-3951) was reacted with methyl iodide in the presence of potassium hydroxide to to give 5-(4-chloro-phenyl)-2-methyl-2H-pyrazole-3-carboxylic acid ethyl ester as colorless crystals and 5-(4-chloro-phenyl)-1-methyl-1H-pyrazole-3-carboxylic acid ethyl ester as colorless oil.

5-(4-chloro-phenyl)-2-methyl-2H-pyrazole-3-carboxylic acid ethyl ester: MS: 265.0 $(M+H)^+$.

5-(4-chloro-phenyl)-1-methyl-1H-pyrazole-3-carboxylic acid ethyl ester: MS: 265.0 $(M+H)^+$.

b] [5-(4-Chloro-phenyl)-2-methyl-2H-pyrazol-3-yl]-methanol

In analogy to the procedure described for example 1 a], 5-(4-chloro-phenyl)-2-methyl-2H-pyrazole-3-carboxylic acid ethyl ester was reduced with lithium aluminium hydride to give [5-(4-chloro-phenyl)-2-methyl-2H-pyrazol-3-yl]-methanol as colorless crystals.

MS: 223.2 $(M+H)^+$.

c] {6-[5-(4-Chloro-phenyl)-2-methyl-2H-pyrazol-3-ylmethoxy]-indol-1-yl}-acetic acid tert-butyl ester In analogy to the procedure described for example 3 c], (6-hydroxy-indol-1-yl)-acetic acid tert-butyl ester (example 1 d]) was reacted with [5-(4-chloro-phenyl)-2-methyl-2H-pyrazol-3-yl]-methanol in the presence of N,N,N',N'-tetramethyl azodicarboxamide and tributylphosphine to give {6-[5-(4-chloro-phenyl)-2-methyl-2H-pyrazol-3-ylmethoxy]-indol-1-yl}-acetic acid tert-butyl ester as colorless oil.

MS: 452.3 $(M+H)^+$.

d] {6-[5-(4-Chloro-phenyl)-2-methyl-2H-pyrazol-3-ylmethoxy]-indol-1-yl}-acetic acid In analogy to the procedure described for example 1 f], {6-[5-(4-chloro-phenyl)-2-methyl-2H-pyrazol-3-ylmethoxy]-indol-1-yl}-acetic acid tert-butyl ester was treated with LiOH to obtain {6-[5-(4-chloro-phenyl)-2-methyl-2H-pyrazol-3-ylmethoxy]-indol-1-yl}-acetic acid as off-white crystals.

MS: 394.1 $(M-H)^-$

Example 6 a] [5-(4-Chloro-phenyl)-1-methyl-1H-pyrazol-3-yl]-methanol

In analogy to the procedure described for example 1 a], 5-(4-chloro-phenyl)-1-methyl-1H-pyrazole-3-carboxylic acid ethyl ester was reduced with lithium aluminium hydride to give [5-(4-chloro-phenyl)-1-methyl-1H-pyrazol-3-yl]-methanol as white solid.

b] {5-[5-(4-Chloro-phenyl)-1-methyl-1H-pyrazol-3-ylmethoxy]-indol-1-yl}-acetic acid tert-butyl ester In analogy to the procedure described for example 3 c], (6-hydroxy-indol-1-yl)-acetic acid tert-butyl ester (example 1 d]) was reacted with [5-(4-chloro-phenyl)-1-methyl-1H-pyrazol-3-yl]-methanol in the presence of N,N,N',N'-tetramethyl azodicarboxamide and tributylphosphine to give {5-[5-(4-chloro-phenyl)-1-methyl-1H-pyrazol-3-ylmethoxy]-indol-1-yl}-acetic acid tert-butyl ester as colorless solid.

MS: 452.3 (M+H)$^+$.

c] {5-[5-(4-Chloro-phenyl)-1-methyl-1H-pyrazol-3-ylmethoxy]-indol-1-yl}-acetic acid In analogy to the procedure described for example 1 f], {5-[5-(4-chloro-phenyl)-1-methyl-1H-pyrazol-3-ylmethoxy]-indol-1-yl}-acetic acid tert-butyl ester was treated with LiOH to obtain {5-[5-(4-chloro-phenyl)-1-methyl-1H-pyrazol-3-ylmethoxy]-indol-1-yl}-acetic acid as colorless solid.

MS: 396.1 (M+H)$^+$.

Example 7 a] 2-Ethyl-5-(4-trifluoromethyl-phenyl)-2H-pyrazole-3-carboxylic acid ethyl ester In analogy to the procedure described for example 2 a], 5-(4-trifluoromethyl-phenyl)-1H-pyrazole-3-carboxylic acid ethyl ester (PCT Int. Appl. (2003), WO 2004000785 A2) was reacted with ethyl iodide in the presence of potassium hydroxide to to give 2-ethyl-5-(4-trifluoromethyl-phenyl)-2H-pyrazole-3-carboxylic acid ethyl ester as colorless crystals.

b] [2-Ethyl-5-(4-trifluoromethyl-phenyl)-2H-pyrazol-3-yl]-methanol

In analogy to the procedure described for example 1 a], 2-ethyl-5-(4-trifluoromethyl-phenyl)-2H-pyrazole-3-carboxylic acid ethyl ester was reduced with lithium aluminium hydride to give [2-ethyl-5-(4-trifluoromethyl-phenyl)-2H-pyrazol-3-yl]-methanol as colorless crystals.

MS: 271.1 (M+H)$^+$.

c] {6-[2-Ethyl-5-(4-trifluoromethyl-phenyl)-2H-pyrazol-3-ylmethoxy]-indol-1-yl}-acetic acid tert-butyl ester In analogy to the procedure described for example 3 c], (6-hydroxy-indol-1-yl)-acetic acid tert-butyl ester (example 1 d]) was reacted with [2-ethyl-5-(4-trifluoromethyl-phenyl)-2H-pyrazol-3-yl]-methanol in the presence of N,N,N',N'-tetramethyl azodicarboxamide and tributylphosphine to give {6-[2-ethyl-5-(4-trifluoromethyl-phenyl)-2H-pyrazol-3-ylmethoxy]-indol-1-yl}-acetic acid tert-butyl ester as colorless oil.

MS: 500.4 (M+H)$^+$.

d] {6-[2-Ethyl-5-(4-trifluoromethyl-phenyl)-2H-pyrazol-3-ylmethoxy]-indol-1-yl}-acetic acid In analogy to the procedure described for example 1 f], {6-[2-ethyl-5-(4-trifluoromethyl-phenyl)-2H-pyrazol-3-ylmethoxy]-indol-1-yl}-acetic acid tert-butyl ester was treated with LiOH to obtain {6-[2-ethyl-5-(4-trifluoromethyl-phenyl)-2H-pyrazol-3-ylmethoxy]-indol-1-yl}-acetic acid as yellow crystals.

MS: 442.3 (M−H)$^-$

Example 8 a] 5-(tert-Butyl-dimethyl-silanyloxymethyl)-1-methyl-3-(4-trifluoromethyl-phenyl)-1H-pyrazole tert-Butylchlorodimethylsilane (32 mg, 0.21 mmol) was added to an ice-cooled solution of [2-methyl-5-(4-trifluoromethyl-phenyl)-2H-pyrazol-3-yl]-methanol (50 mg, 0.2 mmol; example 3 b]) and imidazole (15 mg, 0.22 mmol) in DMF (0.5 ml) under an argon atmosphere. After stirring at ambient temperature for 14 h, the mixture was quenched with ice water (5 ml) and extracted two times with ethyl acetate. The combined extracts were washed with ice water and brine and dried over sodium sulfate. Removal of the solvent under reduced pressure left yellow crystals which were purified by column chromatography (silica gel, heptane/AcOEt) to give 55 mg (0.15 mmol, 76%) of the title compound as colorless crystals.

MS: 371.3 (M+H)$^+$.

b] 4-Bromo-5-(tert-butyl-dimethyl-silanyloxymethyl)-1-methyl-3-(4-trifluoromethyl-phenyl)-1H-pyrazole A solution of 5-(tert-butyl-dimethyl-silanyloxymethyl)-1-methyl-3-(4-trifluoromethyl-phenyl)-1H-pyrazole (162 mg, 437 µmol) in dichloromethane (1.7 ml) was added within 10 min to a mixture of bromine (20 µl, 480 µmol) and sodium carbonate (93 mg, 880 µmol) in dichloromethane (4.3 ml) at 0° C. under an argon atmosphere. After stirring at 0 to 5° C. for 1 h and then at ambient temperature for 1 h, the mixture was quenched with water (5 ml) and extracted two times with dichloromethane. The combined extracts were washed with aqueous saturated NaHSO$_3$ solution and brine/ice water 1/1 and dried over sodium sulfate. Removal of the solvent under reduced pressure left off-white crystals which were purified by column chromatography (silica gel, heptane/AcOEt) to give 90 mg (0.2 mmol, 46%) of the title compound as colorless crystals.

c] [4-Bromo-2-methyl-5-(4-trifluoromethyl-phenyl)-2H-pyrazol-3-yl]-methanol

In analogy to the procedure described for example 2 e], 4-bromo-5-(tert-butyl-dimethyl-silanyloxymethyl)-1-methyl-3-(4-trifluoromethyl-phenyl)-1H-pyrazole was treated with tetrabutylammonium fluoride in THF to yield [4-bromo-2-methyl-5-(4-trifluoromethyl-phenyl)-2H-pyrazol-3-yl]-methanol as yellow oil.

MS: 335.1 (M+H)$^+$.

d] {6-[4-Bromo-2-methyl-5-(4-trifluoromethyl-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [4-bromo-2-methyl-5-(4-trifluoromethyl-phenyl)-2H-pyrazol-3-yl]-methanol in the presence of N,N,N',N'-tetramethyl azodicarboxamide and tributylphosphine to give {6-[4-bromo-2-methyl-5-(4-trifluoromethyl-phenyl)-2H-pyrazol-3-ylmethoxy]-indol-1-yl}-acetic acid ethyl ester as colorless crystals.
MS: 536.3 (M+H)$^+$.

e] {6-[4-Bromo-2-methyl-5-(4-trifluoromethyl-phenyl)-2H-pyrazol-3-ylmethoxy]-indol-1-yl}-acetic acid In analogy to the procedure described for example 1 f], {6-[4-bromo-2-methyl-5-(4-trifluoromethyl-phenyl)-2H-pyrazol-3-ylmethoxy]-indol-1-yl}-acetic acid ethyl ester was treated with LiOH to obtain {6-[4-bromo-2-methyl-5-(4-trifluoromethyl-phenyl)-2H-pyrazol-3-ylmethoxy]-indol-1-yl}-acetic acid as colorless crystals.
MS: 508.2 (M–H)$^-$ Example 9 a] 5-Chloromethyl-1-methyl-3-(4-trifluoromethyl-phenyl)-1H-pyrazole

In analogy to the procedure described for example 1 b], [2-methyl-5-(4-trifluoromethyl-phenyl)-2H-pyrazol-3-yl]-methanol (example 3 b]) was reacted with thionyl chloride in chloroform to yield 5-chloromethyl-1-methyl-3-(4-trifluoromethyl-phenyl)-1H-pyrazole as yellow oil.

b] [2-Methyl-5-(4-trifluoromethyl-phenyl)-2H-pyrazol-3-yl]-acetonitrile

Tetrabutylammonium cyanide (1.96 g, 7 mmol) was added to a solution of 5-chloromethyl-1-methyl-3-(4-trifluoromethyl-phenyl)-1H-pyrazole (1.54 g, 6 mmol) in acetonitrile (35 ml). The solution was stirred at ambient temperature for 16 h, saturated aqueous sodium bicarbonate solution/ice water 1/1 and ethyl acetate were added and the layers were separated. The aqueous layer was extracted with ethyl acetate, the combined organic layers were washed with ice water/brine 1/1, dried over sodium sulfate and the solvent was evaporated in vacuo to give an orange oil which was purified by column chromatography (silica gel, n-heptane/AcOEt) to yield 267 mg (1 mmol, 18%) of the title compound as yellow crystals.
MS: 266.0 (M+H)$^+$.

c] [2-Methyl-5-(4-trifluoromethyl-phenyl)-2H-pyrazol-3-yl]-acetic acid

A mixture of [2-methyl-5-(4-trifluoromethyl-phenyl)-2H-pyrazol-3-yl]-acetonitrile (267 mg, 1 mmol), sodium hydroxide (403 mg, 10 mmol), water (4 ml) and ethanol (4 ml) was stirred vigorously at 85° C. for 14 h. The reaction mixture was poured onto crushed ice and aqueous HCl and extracted three times with ethyl acetate. The combined extracts were washed with water and brine, and dried over anhydrous sodium sulfate. Evaporation of the solvent under reduced pressure gave 286 mg (1 mmol, quant.) of the title compound as off-white crystals.
MS: 283.1 (M–H)$^-$.

d] 2-[2-Methyl-5-(4-trifluoromethyl-phenyl)-2H-pyrazol-3-yl]-ethanol

A solution of [2-methyl-5-(4-trifluoromethyl-phenyl)-2H-pyrazol-3-yl]-acetic acid (286 mg, 1 mmol) in tetrahydrofuran (4 ml) was treated at 0° C. with a 1 M solution of BH$_3$*THF in tetrahydrofuran (2.5 ml, 3 mmol). The cooling bath was removed and the reaction mixture stirred at ambient temperature for 16 h. Careful quenching with MeOH and ice water, twofold extraction with AcOEt, washing with ice water/brine 1/1, drying over magnesium sulfate, and evaporation of the solvent left a crude product which was refluxed for 30 min in MeOH to liberate quantitatively the free alcohol. The solvent was evaporated in vacuo to yield 273 mg (1 mmol, quant.) of the title compound as colorless crystals.
MS: 271.1 (M+H)$^+$.

e] (6-{2-[2-Methyl-5-(4-trifluoromethyl-phenyl)-2H-pyrazol-3-yl]-ethoxy}-indol-1-yl)-acetic acid ethyl ester In analogy to the procedure described for example 3 c], (6-hydroxy-indol-1-yl)-acetic acid ethyl ester (example 2 e]) was reacted with 2-[2-methyl-5-(4-trifluoromethyl-phenyl)-2H-pyrazol-3-yl]-ethanol in the presence of di-tert-butyl azodicarboxylate and triphenylphosphine to give (6-{2-[2-methyl-5-(4-trifluoromethyl-phenyl)-2H-pyrazol-3-yl]-ethoxy}-indol-1-yl)-acetic acid ethyl ester as colorless crystals.
MS: 472.1 (M+H)$^+$.

f] (6-{2-[2-Methyl-5-(4-trifluoromethyl-phenyl)-2H-pyrazol-3-yl]-ethoxy}-indol-1-yl)-acetic acid In analogy to the procedure described in example 1 f], (6-{2-[2-methyl-5-(4-trifluoromethyl-phenyl)-2H-pyrazol-3-yl]-ethoxy}-indol-1-yl)-acetic acid ethyl ester was treated with LiOH to obtain (6-{2-[2-methyl-5-(4-trifluoromethyl-phenyl)-2H-pyrazol-3-yl]-ethoxy}-indol-1-yl)-acetic acid as yellow crystals.
MS: 442.4 (M–H)$^-$ Example 10 a] 5-(tert-Butyl-dimethyl-silanyloxymethyl)-1,4-dimethyl-3-(4-trifluoromethyl-phenyl)-1H-pyrazole A 1.5 M solution of tert-butyllithium in pentane (0.5 ml, 748 µmol) was added dropwise to a solution of 4-bromo-5-(tert-butyl-dimethyl-silanyloxymethyl)-1-methyl-3-(4-trifluoromethyl-phenyl)-1H-pyrazole (280 mg, 623 µmol; example 8 b]) in THF (2 ml) at –78° C. under an argon atmosphere. After 15 min methyl iodide (177 mg, 1.2 mmol) was added at –78° C. The reaction mixture was stirred for another 30 min at –78° C. and then for 2 h at RT. After quenching with saturated aqueous NaHCO$_3$ solution the reaction mixture was partitioned between tert-butyl methyl ether and water. The ether phase was dried over sodium sulfate and concentrated in vacuo to give 240 mg (620 µmol, quant.) 5-(tert-butyl-dimethyl-silanyloxymethyl)-1,4-dimethyl-3-(4-trifluoromethyl-phenyl)-1H-pyrazole as yellow oil which was used in the next step without further purification.

b] [2,4-Dimethyl-5-(4-trifluoromethyl-phenyl)-2H-pyrazol-3-yl]-methanol

In analogy to the procedure described for example 2 e], 5-(tert-butyl-dimethyl-silanyloxymethyl)-1,4-dimethyl-3-(4-trifluoromethyl-phenyl)-1H-pyrazole was treated with tetrabutylammonium fluoride in THF to yield [2,4-dimethyl-5-(4-trifluoromethyl-phenyl)-2H-pyrazol-3-yl]-methanol as yellow oil.

MS: 271.1 $(M+H)^+$.

c] {6-[2,4-Dimethyl-5-(4-trifluoromethyl-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [2,4-dimethyl-5-(4-trifluoromethyl-phenyl)-2H-pyrazol-3-yl]-methanol in the presence of N,N,N',N'-tetramethyl azodicarboxamide and tributylphosphine to give {6-[2,4-dimethyl-5-(4-trifluoromethyl-phenyl)-2H-pyrazol-3-ylmethoxy]-indol-1-yl}-acetic acid ethyl ester as yellow oil.

d] {6-[2,4-Dimethyl-5-(4-trifluoromethyl-phenyl)-2H-pyrazol-3-ylmethoxy]-indol-1-yl}-acetic acid In analogy to the procedure described for example 1 f], {6-[2,4-dimethyl-5-(4-trifluoromethyl-phenyl)-2H-pyrazol-3-ylmethoxy]-indol-1-yl}-acetic acid ethyl ester was treated with LiOH to obtain {6-[2,4-dimethyl-5-(4-trifluoromethyl-phenyl)-2H-pyrazol-3-ylmethoxy]-indol-1-yl}-acetic acid as yellow solid.

MS: 442.2 $(M-H)^-$

Example 11 a] (Z)-2-Hydroxy-4-oxo-4-(4-trifluoromethoxy-phenyl)-but-2-enoic acid ethyl ester A solution of 1-(4-trifluoromethoxy-phenyl)-ethanone (5 g, 24 mmol) and diethyl oxalate (3.25 ml, 24 mmol) in ethanol (5 ml) was added within 20 min to an ice cooled solution of metallic sodium (552 mg, 24 mmol) in ethanol (15 ml) under an argon atmosphere. The cooling bath was removed and the reaction stirred 30 min after reaching ambient temperature. After standing 14 h, the precipitated yellow solid was filtered. The solid was partitioned between 1 M HCl/ice water 1/1 and tert butyl methyl ether. The aqueous layer was extracted two times with tert butyl methyl ether, the combined extracts were washed with brine/ice water 1/1 and dried over sodium sulfate. Evaporation of the solid gave 7.2 g (23.8 mmol, 99%) of the title compound as orange crystals.

MS: 305.0 $(M+H)^+$.

b] 5-(4-Trifluoromethoxy-phenyl)-1H-pyrazole-3-carboxylic acid ethyl ester

In analogy to the procedure described for example 4 b], (Z)-2-hydroxy-4-oxo-4-(4-trifluoromethoxy-phenyl)-but-2-enoic acid ethyl ester was reacted with hydrazine monohydrate in ethanol under reflux conditions to give 5-(4-trifluoromethoxy-phenyl)-1H-pyrazole-3-carboxylic acid ethyl ester as yellow crystals.

MS: 301.0 $(M+H)^+$.

c] 2-Methyl-5-(4-trifluoromethoxy-phenyl)-2H-pyrazole-3-carboxylic acid ethyl ester and 1-methyl-5-(4-trifluoromethoxy-phenyl)-1H-pyrazole-3-carboxylic acid ethyl ester In analogy to the procedure described for example 2 a], 5-(4-trifluoromethoxy-phenyl)-1H-pyrazole-3-carboxylic acid ethyl ester was reacted with methyl iodide in the presence of potassium hydroxide to to give 2-methyl-5-(4-trifluoromethoxy-phenyl)-2H-pyrazole-3-carboxylic acid ethyl ester as white crystals and 1-methyl-5-(4-trifluoromethoxy-phenyl)-1H-pyrazole-3-carboxylic acid ethyl ester as yellow oil.

methyl-5-(4-trifluoromethoxy-phenyl)-2H-pyrazole-3-carboxylic acid ethyl ester: MS: 315.0 $(M+H)^+$.

d] [2-Methyl-5-(4-trifluoromethoxy-phenyl)-2H-pyrazol-3-yl]-methanol

In analogy to the procedure described for example 1 a], 2-methyl-5-(4-trifluoromethoxy-phenyl)-2H-pyrazole-3-carboxylic acid ethyl ester was reduced with lithium aluminium hydride to give [2-methyl-5-(4-trifluoromethoxy-phenyl)-2H-pyrazol-3-yl]-methanol as white crystals.

MS: 273.1 $(M+H)^+$.

e] {6-[2-Methyl-5-(4-trifluoromethoxy-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [2-methyl-5-(4-trifluoromethoxy-phenyl)-2H-pyrazol-3-yl]-methanol in the presence of N,N,N',N'-tetramethyl azodicarboxamide and tributylphosphine to give {6-[2-methyl-5-(4-trifluoromethoxy-phenyl)-2H-pyrazol-3-ylmethoxy]-indol-1-yl}-acetic acid ethyl ester as yellow crystals.

MS: 474.0 $(M+H)^+$.

f] {6-[2-Methyl-5-(4-trifluoromethoxy-phenyl)-2H-pyrazol-3-ylmethoxy]-indol-1-yl}-acetic acid In analogy to the procedure described for example 1 f], {6-[2-methyl-5-(4-trifluoromethoxy-phenyl)-2H-pyrazol-3-ylmethoxy]-indol-1-yl}-acetic acid ethyl ester was treated with LiOH to obtain {6-[2-methyl-5-(4-trifluoromethoxy-phenyl)-2H-pyrazol-3-ylmethoxy]-indol-1-yl}-acetic acid as off-white crystals.

MS: 495.3 $(M+H)^+$.

Example 12 a] 5-(tert-Butyl-dimethyl-silanyloxy)-1H-indole

A solution of 5-hydroxy-indole (5 g, 38 mmol), tert-butyldimethylsilyl chloride (6.13 g, 39.4 mmol) and imidazole (5.37 g, 68.1 mmol) in DMF (50 ml) was stirred for 20 h at RT. Diethyl ether was added and the mixture was washed wih 1N HCl and water. The organic layer was dried over sodium sulfate and concentrated under reduced pressure to give 9.4 g (38 mmol, quant.) 5-(tert-butyl-dimethyl-silanyloxy)-1H-indole.

MS: 248.1 (M+H)+.

b] [5-(tert-Butyl-dimethyl-silanyloxy)-indol-1-yl]-acetic acid ethyl ester

A suspension of 5-(tert-butyl-dimethyl-silanyloxy)-1H-indole (9.2 g, 37.2 mmol), ethyl bromoacetate (4.79 ml, 40.9 mmol) and cesium carbonate (36.4 g, 111.5 mmol) in DMF (140 ml) was stirred for 3 h at RT. Diethyl ether was added and the mixture was washed with 1N HCl and water, and dried over sodium sulfate. The ether phase was concentrated under reduced pressure to give 12.9 g (quant.) of [5-(tert-butyl-dimethyl-silanyloxy)-indol-1-yl]-acetic acid ethyl ester which was used in the next step without further purification.

MS: 334.1 (M+H)+.

c] (5-Hydroxy-indol-1-yl)-acetic acid ethyl ester

To an ice cold solution of [5-(tert-butyl-dimethyl-silanyloxy)-indol-1-yl]-acetic acid ethyl ester (12.9 g, 38.7 mmol) in THF (130 ml) was added tetrabutylammonium fluoride hydrate (12.5 g, 38.7 mmol). The reaction mixture was stirred for 1 h at RT, diluted with diethyl ether and washed with 1N HCl and water. Evaporation of the solvent under reduced pressure gave 7.07 g (32.2 mmol, 83%) (5-hydroxy-indol-1-yl)-acetic acid ethyl ester.

MS: 220.1 (M+H)+.

d] {5-[2-Methyl-5-(4-trifluoromethoxy-phenyl)-2H-pyrazol-3-ylmethoxy]-indol-1-yl}-acetic acid ethyl ester In analogy to the procedure described for example 3 c], (5-hydroxy-indol-1-yl)-acetic acid ethyl ester was reacted with [2-methyl-5-(4-trifluoromethoxy-phenyl)-2H-pyrazol-3-yl]-methanol in the presence of N,N,N',N'-tetramethyl azodicarboxamide and tributylphosphine to give {5-[2-methyl-5-(4-trifluoromethoxy-phenyl)-2H-pyrazol-3-ylmethoxy]-indol-1-yl}-acetic acid ethyl ester as colorless oil.

MS: 474.0 (M+H)+.

e] {5-[2-Methyl-5-(4-trifluoromethoxy-phenyl)-2H-pyrazol-3-ylmethoxy]-indol-1-yl}-acetic acid In analogy to the procedure described for example 1 f], {5-[2-methyl-5-(4-trifluoromethoxy-phenyl)-2H-pyrazol-3-ylmethoxy]-indol-1-yl}-acetic acid ethyl ester was treated with LiOH to obtain {5-[2-methyl-5-(4-trifluoromethoxy-phenyl)-2H-pyrazol-3-ylmethoxy]-indol-1-yl}-acetic acid as yellow foam.

MS: 446.0 (M+H)+.

Example 13 a] 2-(2,2,2-Trifluoro-ethyl)-5-(4-trifluoromethyl-phenyl)-2H-pyrazole-3-carboxylic acid ethyl ester Sodium hydride (55% dispersion in mineral oil, 203 mg, 5 mmol) was added to an ice cooled solution of 5-(4-trifluoromethyl-phenyl)-1H-pyrazole-3-carboxylic acid ethyl ester (1 g, 4 mmol; PCT Int. Appl. (2003), WO 2004000785 A2) in DMF (60 ml) under an argon atmosphere. The solution was stirred for 10 min at 0° C. and for 40 min at ambient temperature. Trifluoroethyltriflate (1.07 g, 5 mmol) was added and the mixture was stirred for 3 h at ambient temperature. The solution was cooled to 0° C., 1 N HCl/ice water 1/2 and dichloromethane were added. The aqueous layer was extracted two times with dichloromethane, the combined extracts were washed with brine/ice water 1/1 and dried over sodium sulfate. Evaporation of the solvent under reduced pressure gave yellow crystals which were purified by column chromatography (silica gel, n-heptane/AcOEt) to yield 833 mg (2.27 mmol, 65%) of the title compound as colorless crystals.

b] [2-(2,2,2-Trifluoro-ethyl)-5-(4-trifluoromethyl-phenyl)-2H-pyrazol-3-yl]-methanol In analogy to the procedure described for example 1 a], 2-(2,2,2-trifluoro-ethyl)-5-(4-trifluoromethyl-phenyl)-2H-pyrazole-3-carboxylic acid ethyl ester was reduced with lithium aluminium hydride to give [2-(2,2,2-trifluoro-ethyl)-5-(4-trifluoromethyl-phenyl)-2H-pyrazol-3-yl]-methanol as colorless crystals.

MS: 324.0 (M)+.

c] {6-[2-(2,2,2-Trifluoro-ethyl)-5-(4-trifluoromethyl-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [2-(2,2,2-trifluoro-ethyl)-5-(4-trifluoromethyl-phenyl)-2H-pyrazol-3-yl]-methanol in the presence of N,N,N',N'-tetramethyl azodicarboxamide and tributylphosphine to give {6-[2-(2,2,2-trifluoro-ethyl)-5-(4-trifluoromethyl-phenyl)-2H-pyrazol-3-ylmethoxy]-indol-1-yl}-acetic acid ethyl ester as colorless oil.

MS: 526.0 (M+H)+.

d] {6-[2-(2,2,2-Trifluoro-ethyl)-5-(4-trifluoromethyl-phenyl)-2H-pyrazol-3-ylmethoxy]-indol-1-yl}-acetic acid In analogy to the procedure described for example 1 f], {6-[2-(2,2,2-trifluoro-ethyl)-5-(4-trifluoromethyl-phenyl)-2H-pyrazol-3-ylmethoxy]-indol-1-yl}-acetic acid ethyl ester was treated with LiOH to obtain {6-[2-(2,2,2-trifluoro-ethyl)-5-(4-trifluoromethyl-phenyl)-2H-pyrazol-3-ylmethoxy]-indol-1-yl}-acetic acid as off-white crystals.

MS: 498.3 (M+H)+.

Example 14 a] 6-Benzyloxy-4-methyl-1H-indole-2-carboxylic acid

A 2 M solution of potassium hydroxide in ethanol (0.48 ml, 0.97 mmol) was added to a solution of 6-benzyloxy-4-methyl-1H-indole-2-carboxylic acid ethyl ester (100 mg, 0.32 mmol; PCT Int. Appl. (2001), WO 2001044186 A1) in ethanol (1 ml). The mixture was heated at reflux for 1.5 h, acidified with 1 N HCl and extracted two times with ethyl acetate. The combined extracts were washed with brine and dried over sodium sulfate. Evaporation of the solvent under reduced pressure gave 90 mg (0.32 mmol, 99%) of the title compound as yellow crystals.

b] 6-Benzyloxy-4-methyl-1H-indole

A suspension of 6-benzyloxy-4-methyl-1H-indole-2-carboxylic acid (28 mg, 0.95 mmol) and copper chromite (19 mg, 0.06 mmol) in quinoline (1.4 ml) was heated at 230° C. (bath temp.) for 1.5 h. The mixture was poured onto 2 N HCl/ice water 1/1 and extracted three times with ethyl acetate. The combined extracts were washed with saturated aqueous $NaHCO_3$ solution and brine and dried over sodium sulfate. Evaporation of the solvent under reduced pressure left a black oil which was purified by column chromatography (silica gel, n-heptane/AcOEt) to yield 90 mg (0.32 mmol, 34%) of the title compound as brown oil.

MS: 252.4 $(M+H)^+$.

c] (6-Benzyloxy-4-methyl-indol-1-yl)-acetic acid tert-butyl ester

In analogy to the procedure described in example 1 c], 6-benzyloxy-4-methyl-1H-indole was reacted with bromoacetic acid tert-butyl ester in the presence of cesium carbonate in DMF to obtain (6-benzyloxy-4-methyl-indol-1-yl)-acetic acid tert-butyl ester as yellow oil.

MS: 352.1 $(M+H)^+$.

d] (6-Hydroxy-4-methyl-indol-1-yl)-acetic acid tert-butyl ester

A solution of (6-benzyloxy-4-methyl-indol-1-yl)-acetic acid tert-butyl ester (140 mg, 0.4 mmol) in ethanol (14 ml) was hydrogenated over 10% palladium on charcoal (14 mg) at ambient temperature for 3 h. The catalyst was filtered off, the solvent evaporated under reduced pressure to give 100 mg (0.38 mmol, 96%) of the title compound as brown oil which was used in the next step without further purification.

MS: 279.3 $(M+NH_4)^+$.

e] {4-Methyl-6-[2-methyl-5-(4-trifluoromethoxy-phenyl)-2H-pyrazol-3-ylmethoxy]-indol-1-yl}-acetic acid tert-butyl ester In analogy to the procedure described for example 3 c], (6-hydroxy-4-methyl-indol-1-yl)-acetic acid tert-butyl ester was reacted with [2-methyl-5-(4-trifluoromethoxy-phenyl)-2H-pyrazol-3-yl]-methanol in the presence of N,N,N',N'-tetramethyl azodicarboxamide and tributylphosphine to give {4-methyl-6-[2-methyl-5-(4-trifluoromethoxy-phenyl)-2H-pyrazol-3-ylmethoxy]-indol-1-yl}-acetic acid tert-butyl ester as colorless liquid.

MS: 516.5 $(M+H)^+$.

f] {4-Methyl-6-[2-methyl-5-(4-trifluoromethoxy-phenyl)-2H-pyrazol-3-ylmethoxy]-indol-1-yl}-acetic acid In analogy to the procedure described for example 1 f], {4-methyl-6-[2-methyl-5-(4-trifluoromethoxy-phenyl)-2H-pyrazol-3-ylmethoxy]-indol-1-yl}-acetic acid tert-butyl ester was treated with LiOH to obtain {4-methyl-6-[2-methyl-5-(4-trifluoromethoxy-phenyl)-2H-pyrazol-3-ylmethoxy]-indol-1-yl}-acetic acid as colorless solid.

MS: 460.4 $(M+H)^+$.

Example 15 a] 2-(2,2,2-Trifluoro-ethyl)-5-(4-trifluoromethoxy-phenyl)-2H-pyrazole-3-carboxylic acid ethyl ester In analogy to the procedure described for example 13 a], 5-(4-trifluoromethoxy-phenyl)-1H-pyrazole-3-carboxylic acid ethyl ester (example 11 b]) was reacted with trifluoro-ethyltriflate to give 2-(2,2,2-trifluoro-ethyl)-5-(4-trifluoromethoxy-phenyl)-2H-pyrazole-3-carboxylic acid ethyl ester as colorless solid.

MS: 382.1 $(M)^+$.

b] [2-(2,2,2-Trifluoro-ethyl)-5-(4-trifluoromethoxy-phenyl)-2H-pyrazol-3-yl]-methanol In analogy to the procedure described for example 1 a], 2-(2,2,2-trifluoro-ethyl)-5-(4-trifluoromethoxy-phenyl)-2H-pyrazole-3-carboxylic acid ethyl ester was reduced with lithium aluminium hydride to give [2-(2,2,2-trifluoro-ethyl)-5-(4-trifluoromethoxy-phenyl)-2H-pyrazol-3-yl]-methanol as colorless solid.

MS: 341.0 $(M+H)^+$.

c] {6-[2-(2,2,2-Trifluoro-ethyl)-5-(4-trifluoromethoxy-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [2-(2,2,2-trifluoro-ethyl)-5-(4-trifluoromethoxy-phenyl)-2H-pyrazol-3-yl]-methanol in the presence of N,N,N',N'-tetramethyl azodicarboxamide and tributylphosphine to give {6-[2-(2,2,2-trifluoro-ethyl)-5-(4-trifluoromethoxy-phenyl)-2H-pyrazol-3-ylmethoxy]-indol-1-yl}-acetic acid ethyl ester as yellow oil.

MS: 542.2 $(M+H)^+$.

d] {6-[2-(2,2,2-Trifluoro-ethyl)-S-(4-trifluoromethoxy-phenyl)-2H-pyrazol-3-ylmethoxy]-indol-1-yl}-acetic acid In analogy to the procedure described for example 1 f], {6-[2-(2,2,2-trifluoro-ethyl)-5-(4-trifluoromethoxy-phenyl)-2H-pyrazol-3-ylmethoxy]-indol-1-yl}-acetic acid ethyl ester was treated with LiOH to obtain {6-[2-(2,2,2-trifluoro-ethyl)-5-(4-trifluoromethoxy-phenyl)-2H-pyrazol-3-ylmethoxy]-indol-1-yl}-acetic acid as brown oil.

MS: 514.2 $(M+H)^+$.

Example 16 a] [1-Methyl-5-(4-trifluoromethoxy-phenyl)-1H-pyrazol-3-yl]-methanol

In analogy to the procedure described for example 1 a], 1-methyl-5-(4-trifluoromethoxy-phenyl)-1H-pyrazole-3-carboxylic acid ethyl ester (example 11 c]) was reduced with lithium aluminium hydride to give [1-methyl-5-(4-trifluoromethoxy-phenyl)-1H-pyrazol-3-yl]-methanol as brown solid.

MS: 273.0 $(M+H)^+$.

b] {6-[1-Methyl-5-(4-trifluoromethoxy-phenyl)-1H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [1-methyl-5-(4-trifluoromethoxy-phenyl)-1H-pyrazol-3-yl]-methanol in the presence of N,N,N',N'-tetramethyl azodicarboxamide and tributylphosphine to give {6-[1-methyl-5-(4-trifluoromethoxy-phenyl)-1H-pyrazol-3-ylmethoxy]-indol-1-yl}-acetic acid ethyl ester as colorless solid.
MS: 474.4 (M+H)$^+$.

c] {6-[1-Methyl-5-(4-trifluoromethoxy-phenyl)-1H-pyrazol-3-ylmethoxy]-indol-1-yl}-acetic acid In analogy to the procedure described for example 1 f], {6-[1-methyl-5-(4-trifluoromethoxy-phenyl)-1H-pyrazol-3-ylmethoxy]-indol-1-yl}-acetic acid ethyl ester was treated with LiOH to obtain {6-[1-methyl-5-(4-trifluoromethoxy-phenyl)-1H-pyrazol-3-ylmethoxy]-indol-1-yl}-acetic acid as colorless solid.
MS: 446.0 (M+H)$^+$.

Example 17 a] (Z)-4-(3,4-Dichloro-phenyl)-2-hydroxy-4-oxo-but-2-enoic acid ethyl ester

In analogy to the procedure described for example 11 a], 1-(3,4-dichloro-phenyl)-ethanone was reacted with diethyl oxalate in the presence of metallic sodium to give (Z)-4-(3,4-dichloro-phenyl)-2-hydroxy-4-oxo-but-2-enoic acid ethyl ester as off-white solid.
MS: 289.0 (M+H)$^+$.

b] 5-(3,4-Dichloro-phenyl)-2-methyl-2H-pyrazole-3-carboxylic acid ethyl ester and 5-(3,4-dichloro-phenyl)-1-methyl-1H-pyrazole-3-carboxylic acid ethyl ester In analogy to the procedure described for example 4 b], (Z)-4-(3,4-dichloro-phenyl)-2-hydroxy-4-oxo-but-2-enoic acid ethyl ester was reacted with methylhydrazine in ethanol under reflux conditions to give 5-(3,4-dichloro-phenyl)-2-methyl-2H-pyrazole-3-carboxylic acid ethyl ester as colorless crystals and 5-(3,4-dichloro-phenyl)-1-methyl-1H-pyrazole-3-carboxylic acid ethyl ester as colorless crystals.
5-(3,4-dichloro-phenyl)-2-methyl-2H-pyrazole-3-carboxylic acid ethyl ester: MS: 299.1 (M+H)$^+$.

c] [5-(3,4-Dichloro-phenyl)-2-methyl-2H-pyrazol-3-yl]-methanol

In analogy to the procedure described for example 1 a], 5-(3,4-dichloro-phenyl)-2-methyl-2H-pyrazole-3-carboxylic acid ethyl ester was reduced with lithium aluminium hydride to give [5-(3,4-dichloro-phenyl)-2-methyl-2H-pyrazol-3-yl]-methanol as white solid.
MS: 256.0 (M)$^+$.

d] {6-[5-(3,4-Dichloro-phenyl)-2-methyl-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [5-(3,4-dichloro-phenyl)-2-methyl-2H-pyrazol-3-yl]-methanol in the presence of N,N,N',N'-tetramethyl azodicarboxamide and tributylphosphine to give {6-[5-(3,4-dichloro-phenyl)-2-methyl-2H-pyrazol-3-ylmethoxy]-indol-1-yl}-acetic acid ethyl ester as colorless oil.
MS: 458.2 (M+H)$^+$.

e] {6-[5-(3,4-Dichloro-phenyl)-2-methyl-2H-pyrazol-3-ylmethoxy]-indol-1-yl}-acetic acid ethyl ester In analogy to the procedure described for example 1 f], {6-[5-(3,4-dichloro-phenyl)-2-methyl-2H-pyrazol-3-ylmethoxy]-indol-1-yl}-acetic acid ethyl ester was treated with LiOH to obtain {6-[5-(3,4-dichloro-phenyl)-2-methyl-2H-pyrazol-3-ylmethoxy]-indol-1-yl}-acetic acid ethyl ester as brown crystals.
MS: 430.4 (M+H)$^+$.

Example 18 a] (Z)-4-(4-Fluoro-3-trifluoromethyl-phenyl)-2-hydroxy-4-oxo-but-2-enoic acid ethyl ester In analogy to the procedure described for example 11 a], 1-(4-fluoro-3-trifluoromethyl-phenyl)-ethanone was reacted with diethyl oxalate in the presence of metallic sodium to give (Z)-4-(4-fluoro-3-trifluoromethyl-phenyl)-2-hydroxy-4-oxo-but-2-enoic acid ethyl ester as colorless solid.
MS: 307.1 (M+H)$^+$.

b] 5-(4-Fluoro-3-trifluoromethyl-phenyl)-2-methyl-2H-pyrazole-3-carboxylic acid ethyl ester and 5-(4-Fluoro-3-trifluoromethyl-phenyl)-1-methyl-1H-pyrazole-3-carboxylic acid ethyl ester In analogy to the procedure described for example 4 b], (Z)-4-(4-fluoro-3-trifluoromethyl-phenyl)-2-hydroxy-4-oxo-but-2-enoic acid ethyl ester was reacted with methylhydrazine in ethanol under reflux conditions to give 5-(4-fluoro-3-trifluoromethyl-phenyl)-2-methyl-2H-pyrazole-3-carboxylic acid ethyl ester as colorless crystals and 5-(4-fluoro-3-trifluoromethyl-phenyl)-1-methyl-1H-pyrazole-3-carboxylic acid ethyl ester as colorless crystals.
5-(4-fluoro-3-trifluoromethyl-phenyl)-2-methyl-2H-pyrazole-3-carboxylic acid ethyl ester: MS: 317.0 (M+H)$^+$.

c] [5-(4-Fluoro-3-trifluoromethyl-phenyl)-2-methyl-2H-pyrazol-3-yl]-methanol

In analogy to the procedure described for example 1 a], 5-(4-fluoro-3-trifluoromethyl-phenyl)-2-methyl-2H-pyrazole-3-carboxylic acid ethyl ester was reduced with lithium aluminium hydride to give [5-(4-fluoro-3-trifluoromethyl-phenyl)-2-methyl-2H-pyrazol-3-yl]-methanol as white solid.
MS: 275.3 (M+H)$^+$.

d] {6-[5-(4-Fluoro-3-trifluoromethyl-phenyl)-2-methyl-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [5-(4-fluoro-3-trifluoromethyl-phenyl)-2-methyl-2H-pyrazol-3-yl]-methanol in the presence of N,N,N',N'-tetramethyl azodicarboxamide and tributylphosphine to give {6-[5-(4-fluoro-3-trifluoromethyl-phenyl)-2-methyl-2H-pyrazol-3-ylmethoxy]-indol-1-yl}-acetic acid ethyl ester as white solid.

MS: 476.0 (M+H)+.

e] {6-[5-(4-Fluoro-3-trifluoromethyl-phenyl)-2-methyl-2H-pyrazol-3-ylmethoxy]-indol-1-yl}-acetic acid In analogy to the procedure described for example 1 f], {6-[5-(4-fluoro-3-trifluoromethyl-phenyl)-2-methyl-2H-pyrazol-3-ylmethoxy]-indol-1-yl}-acetic acid ethyl ester was treated with LiOH to obtain {6-[5-(4-fluoro-3-trifluoromethyl-phenyl)-2-methyl-2H-pyrazol-3-ylmethoxy]-indol-1-yl}-acetic acid as brown solid.

MS: 448.1 (M+H)+.

Example 19 a] 5-Chloromethyl-1-methyl-3-(4-trifluoromethoxy-phenyl)-1H-pyrazole

In analogy to the procedure described for example 1 b], [2-methyl-5-(4-trifluoromethoxy-phenyl)-2H-pyrazol-3-yl]-methanol (example 11 d]) was reacted with thionyl chloride in chloroform to yield 5-chloromethyl-1-methyl-3-(4-trifluoromethoxy-phenyl)-1H-pyrazole as colorless oil.

MS: 291.0 (M+H)+.

b] [2-Methyl-5-(4-trifluoromethoxy-phenyl)-2H-pyrazol-3-yl]-acetonitrile

In analogy to the procedure described for example 9 b], 5-chloromethyl-1-methyl-3-(4-trifluoromethoxy-phenyl)-1H-pyrazole was reacted with tetrabutylammonium cyanide in acetonitrile to give [2-methyl-5-(4-trifluoromethoxy-phenyl)-2H-pyrazol-3-yl]-acetonitrile as yellow solid.

MS: 300.4 (M+NH4)+.

c] [2-Methyl-5-(4-trifluoromethoxy-phenyl)-2H-pyrazol-3-yl]-acetic acid

In analogy to the procedure described for example 9 c], [2-methyl-5-(4-trifluoromethoxy-phenyl)-2H-pyrazol-3-yl]-acetonitrile was treated with sodium hydroxide in water/ethanol 1/1 at 85° C. to give [2-methyl-5-(4-trifluoromethoxy-phenyl)-2H-pyrazol-3-yl]-acetic acid as off-white solid.

MS: 301.0 (M+H)+.

d] 2-[2-Methyl-5-(4-trifluoromethoxy-phenyl)-2H-pyrazol-3-yl]-ethanol

In analogy to the procedure described for example 9 c], [2-methyl-5-(4-trifluoromethoxy-phenyl)-2H-pyrazol-3-yl]-acetic acid was reduced with a 1 M solution of BH3*THF in tetrahydrofuran to give 2-[2-methyl-5-(4-trifluoromethoxy-phenyl)-2H-pyrazol-3-yl]-ethanol as colorless crystals.

MS: 287.0 (M+H)+.

e] (6-{2-[2-Methyl-5-(4-trifluoromethoxy-phenyl)-2H-pyrazol-3-yl]-ethoxy}-indol-1-yl)-acetic acid ethyl ester In analogy to the procedure described for example 3 c], (6-hydroxy-indol-1-yl)-acetic acid ethyl ester (example 2 e]) was reacted with 2-[2-methyl-5-(4-trifluoromethoxy-phenyl)-2H-pyrazol-3-yl]-ethanol in the presence of di-tert-butyl azodicarboxylate and triphenylphosphine to give (6-{2-[2-methyl-5-(4-trifluoromethoxy-phenyl)-2H-pyrazol-3-yl]-ethoxy}-indol-1-yl)-acetic acid ethyl ester as colorless crystals.

MS: 488.1 (M+H)+.

f] (6-{2-[2-Methyl-5-(4-trifluoromethoxy-phenyl)-2H-pyrazol-3-yl]-ethoxy}-indol-1-yl)-acetic acid In analogy to the procedure described in example 1 f], (6-{2-[2-methyl-5-(4-trifluoromethoxy-phenyl)-2H-pyrazol-3-yl]-ethoxy}-indol-1-yl)-acetic acid ethyl ester was treated with LiOH to obtain (6-{2-[2-methyl-5-(4-trifluoromethoxy-phenyl)-2H-pyrazol-3-yl]-ethoxy}-indol-1-yl)-acetic acid as colorless crystals.

MS: 460.4 (M+H)+.

Example 20 a] 5-Iodomethyl-1-methyl-3-(4-trifluoromethoxy-phenyl)-1H-pyrazole

A suspension of 5-chloromethyl-1-methyl-3-(4-trifluoromethoxy-phenyl)-1H-pyrazole (3.2 g, 11 mmol; example 19 a]) and sodium iodide (8.25 g, 55 mmol) in acetone (56 ml) was heated under reflux conditions for 30 min. Tert butyl methyl ether was added, the solid was filtered off and the filtrate was brought to dryness under reduced pressure. The residue was dissolved in tert butyl methyl ether, washed with ice water/brine 1/1 and the aqueous layer was extracted two times with tert butyl methyl ether. The combined extracts were washed with aqueous sodium thiosulfate solution and brine and dried over sodium sulfate. The solvent was removed under reduced pressure to give the title compound as yellow oil which was used in the next step without further purification.

b] 3-[2-Methyl-5-(4-trifluoromethoxy-phenyl)-2H-pyrazol-3-yl]-prop ionic acid ethyl ester A solution of lithium diisopropylamide (16.5 ml of a 2 M solution in tetrahydrofuran/heptane/ethylbenzol, 33 mmol) in tetrahydrofuran (25 ml) was cooled to −78° C. Within 30 min a solution of ethyl acetate (3.77 ml, 38 mmol) in tetrahydrofuran (10 ml) was added. The solution was stirred for 45 min at −78° C., DMPU (6.63 ml, 55 mmol) was added within 20 min and the mixture was kept for additional 30 min at −78° C. Within 20 min a solution of 5-iodomethyl-1-methyl-3-(4-trifluoromethoxy-phenyl)-1H-pyrazole (4.2 g, 11 mmol) in tetrahydrofuran (25 ml) was added. The solution was stirred for 40 min at −78° C., the cooling bath was removed and stirring was continued for 1 h. The reaction mixture was poored onto aqueous NH4Cl solution/ice water and extracted two times with ethyl acetate. The combined extracts were washed three times with ice water/brine and dried over sodium sulfate. The solvent was removed under reduced pressure to give an orange oil which was purified by column chromatography (silica gel, heptane/AcOEt) to give 1.5 g (4.4 mmol, 40%) of the title compound as yellow oil.

MS: 343.1 (M+H)+.

c] 3-[2-Methyl-5-(4-trifluoromethoxy-phenyl)-2H-pyrazol-3-yl]-propan-1-ol

In analogy to the procedure described for example 1 a], 3-[2-methyl-5-(4-trifluoromethoxy-phenyl)-2H-pyrazol-3-yl]-propionic acid ethyl ester was reduced with lithium aluminium hydride in diethyl ether to give 3-[2-methyl-5-(4-trifluoromethoxy-phenyl)-2H-pyrazol-3-yl]-propan-1-ol as yellow oil.
MS: 300.2 (M)$^+$.

d] (6-{3-[2-Methyl-5-(4-trifluoromethoxy-phenyl)-2H-pyrazol-3-yl]-propoxy}-indol-1-yl)-acetic acid ethyl ester In analogy to the procedure described for example 3 c], (6-hydroxy-indol-1-yl)-acetic acid ethyl ester (example 2 e]) was reacted with 3-[2-methyl-5-(4-trifluoromethoxy-phenyl)-2H-pyrazol-3-yl]-propan-1-ol in the presence of N,N,N',N'-tetramethyl azodicarboxamide and tributylphosphine to give (6-{3-[2-methyl-5-(4-trifluoromethoxy-phenyl)-2H-pyrazol-3-yl]-propoxy}-indol-1-yl)-acetic acid ethyl ester as colorless oil.
MS: 502.5 (M+H)$^+$.

e] (6-{3-[2-Methyl-5-(4-trifluoromethoxy-phenyl)-2H-pyrazol-3-yl]-propoxy}-indol-1-yl)-acetic acid In analogy to the procedure described for example 1 f], (6-{3-[2-methyl-5-(4-trifluoromethoxy-phenyl)-2H-pyrazol-3-yl]-propoxy}-indol-1-yl)-acetic acid ethyl ester was treated with LiOH to obtain (6-{3-[2-methyl-5-(4-trifluoromethoxy-phenyl)-2H-pyrazol-3-yl]-propoxy}-indol-1-yl)-acetic acid ethyl ester as yellow foam.
MS: 472.1 (M−H)$^−$.

Example 21 a] 5-Chloromethyl-1-(2,2,2-trifluoro-ethyl)-3-(4-trifluoromethoxy-phenyl)-1H-pyrazole In analogy to the procedure described for example 1 b], [2-(2,2,2-trifluoro-ethyl)-5-(4-trifluoromethoxy-phenyl)-2H-pyrazol-3-yl]-methanol (example 15 b]) was reacted with thionyl chloride in chloroform to yield 5-chloromethyl-1-(2,2,2-trifluoro-ethyl)-3-(4-trifluoromethoxy-phenyl)-1H-pyrazole as colorless oil.
MS: 359.0 (M+H)$^+$.

b] [2-(2,2,2-Trifluoro-ethyl)-5-(4-trifluoromethoxy-phenyl)-2H-pyrazol-3-yl]-acetonitrile In analogy to the procedure described for example 9 b], 5-chloromethyl-1-(2,2,2-trifluoro-ethyl)-3-(4-trifluoromethoxy-phenyl)-1H-pyrazole was reacted with tetrabutylammonium cyanide in acetonitrile to give [2-(2,2,2-trifluoro-ethyl)-5-(4-trifluoromethoxy-phenyl)-2H-pyrazol-3-yl]-acetonitrile as yellow oil.
MS: 350.3 (M+NH$_4$)$^+$.

c] [2-(2,2,2-Trifluoro-ethyl)-5-(4-trifluoromethoxy-phenyl)-2H-pyrazol-3-yl]-acetic acid In analogy to the procedure described for example 9 c], [2-(2,2,2-trifluoro-ethyl)-5-(4-trifluoromethoxy-phenyl)-2H-pyrazol-3-yl]-acetonitrile was treated with sodium hydroxide in water/ethanol 1/1 at 85° C. to give [2-(2,2,2-trifluoro-ethyl)-5-(4-trifluoromethoxy-phenyl)-2H-pyrazol-3-yl]-acetic acid as brown crystals.
MS: 369.1 (M+H)$^+$.

d] 2-[2-(2,2,2-Trifluoro-ethyl)-5-(4-trifluoromethoxy-phenyl)-2H-pyrazol-3-yl]-ethanol In analogy to the procedure described for example 9 c], [2-(2,2,2-trifluoro-ethyl)-5-(4-trifluoromethoxy-phenyl)-2H-pyrazol-3-yl]-acetic acid was reduced with a 1 M solution of BH$_3$*THF in tetrahydrofuran to give 2-[2-(2,2,2-trifluoro-ethyl)-5-(4-trifluoromethoxy-phenyl)-2H-pyrazol-3-yl]-ethanol as colorless oil.
MS: 355.3 (M+H)$^+$.

e] (6-{2-[2-(2,2,2-Trifluoro-ethyl)-5-(4-trifluoromethoxy-phenyl)-2H-pyrazol-3-yl]-ethoxy}-indol-1-yl)-acetic acid ethyl ester In analogy to the procedure described for example 3 c], (6-hydroxy-indol-1-yl)-acetic acid ethyl ester (example 2 e]) was reacted with 2-[2-(2,2,2-trifluoro-ethyl)-5-(4-trifluoromethoxy-phenyl)-2H-pyrazol-3-yl]-ethanol in the presence of di-tert-butyl azodicarboxylate and triphenylphosphine to give (6-{2-[2-(2,2,2-trifluoro-ethyl)-5-(4-trifluoromethoxy-phenyl)-2H-pyrazol-3-yl]-ethoxy}-indol-1-yl)-acetic acid ethyl ester as colorless oil.
MS: 556.3 (M+H)$^+$.

f] (6-{2-[2-(2,2,2-Trifluoro-ethyl)-5-(4-trifluoromethoxy-phenyl)-2H-pyrazol-3-yl]-ethoxy}-indol-1-yl)-acetic acid In analogy to the procedure described in example 1 f], (6-{2-[2-(2,2,2-trifluoro-ethyl)-5-(4-trifluoromethoxy-phenyl)-2H-pyrazol-3-yl]-ethoxy}-indol-1-yl)-acetic acid ethyl ester was treated with LiOH to obtain (6-{2-[2-(2,2,2-trifluoro-ethyl)-5-(4-trifluoromethoxy-phenyl)-2H-pyrazol-3-yl]-ethoxy}-indol-1-yl)-acetic acid as off-white solid.
MS: 528.0 (M+H)$^+$.

Example 22 a] [rac]-2-{6-[2-(2,2,2-Trifluoro-ethyl)-5-(4-trifluoromethoxy-phenyl)-2H-pyrazol-3-ylmethoxy]-indol-1-yl}-propionic acid ethyl ester In analogy to the procedure described for example 3 c], [rac]-2-(6-hydroxy-indol-1-yl)-propionic acid ethyl ester (J. E. D. Barton, D. Cartwright, C. J. Mathews, Brit. UK Pat. Appl. (1992), GB 2253848 A1) was reacted with [2-(2,2,2-trifluoro-ethyl)-5-(4-trifluoromethoxy-phenyl)-2H-pyrazol-3-yl]-methanol (example 15 b]) in the presence of N,N,N',N'-tetramethyl azodicarboxamide and tributylphosphine to give [rac]-2-{6-[2-(2,2,2-trifluoro-ethyl)-5-(4-trifluoromethoxy-phenyl)-2H-pyrazol-3-ylmethoxy]-indol-1-yl}-propionic acid ethyl ester as colorless oil.
MS: 556.5 (M+H)$^+$.

b] [rac]-2-{6-[2-(2,2,2-Trifluoro-ethyl)-5-(4-trifluoromethoxy-phenyl)-2H-pyrazol-3-ylmethoxy]-indol-1-yl}-propionic acid In analogy to the procedure described in example 1 f], [rac]-2-{6-[2-(2,2,2-trifluoro-ethyl)-5-(4-trifluoromethoxy-phenyl)-2H-pyrazol-3-ylmethoxy]-indol-1-yl}-propionic acid ethyl ester was treated with LiOH to obtain [rac]-2-{6-

[2-(2,2,2-trifluoro-ethyl)-5-(4-trifluoromethoxy-phenyl)-2H-pyrazol-3-ylmethoxy]-indol-1-yl}-propionic acid as colorless foam.

MS: 528.3 (M+H)+.

Example 23 a] 2-Difluoromethyl-5-(4-trifluoromethoxy-phenyl)-2H-pyrazole-3-carboxylic acid ethyl ester and 1-Difluoromethyl-5-(4-trifluoromethoxy-phenyl)-1H-pyrazole-3-carboxylic acid ethyl ester Chlorodifluoromethane (28.6 g, 331 mmol) was introduced to a suspension of 5-(4-trifluoromethoxy-phenyl)-1H-pyrazole-3-carboxylic acid ethyl ester (2 g, 7 mmol; example 11 b]) and anhydrous potassium carbonate (2.76 g, 20 mmol) in dry N,N-dimethylformamide (120 ml) at 90° C. for 2 h. After cooling, the mixture was poured into ice water (400 ml) and extracted four times with dichloromethane. The combined extracts were washed two times with ice water/brine and dried over sodium sulfate. The solvent was removed under reduced pressure to give a yellow solid which was purified by column chromatography (silica gel, heptane/AcOEt) to give 281 mg (0.8 mmol, 12%) 2-difluoromethyl-5-(4-trifluoromethoxy-phenyl)-2H-pyrazole-3-carboxylic acid ethyl ester as white solid and 1.29 g (3.7 mmol, 55%) 1-difluoromethyl-5-(4-trifluoromethoxy-phenyl)-1H-pyrazole-3-carboxylic acid ethyl ester as white solid.

difluoromethyl-5-(4-trifluoromethoxy-phenyl)-2H-pyrazole-3-carboxylic acid ethyl ester: MS: 351.3 (M+H)+.

difluoromethyl-5-(4-trifluoromethoxy-phenyl)-1H-pyrazole-3-carboxylic acid ethyl ester: MS: 351.3 (M+H)+.

b] [2-Difluoromethyl-5-(4-trifluoromethoxy-phenyl)-2H-pyrazol-3-yl]-methanol

In analogy to the procedure described for example 1 a], 2-difluoromethyl-5-(4-trifluoromethoxy-phenyl)-2H-pyrazole-3-carboxylic acid ethyl ester was reduced with lithium aluminium hydride to give [2-difluoromethyl-5-(4-trifluoromethoxy-phenyl)-2H-pyrazol-3-yl]-methanol as white solid.

MS: 309.4 (M+H)+.

c] {6-[2-Difluoromethyl-5-(4-trifluoromethoxy-phenyl)-2H-pyrazol-3-ylmethoxy]-indol-1-yl}-acetic acid ethyl ester In analogy to the procedure described for example 3 c], (6-hydroxy-indol-1-yl)-acetic acid ethyl ester (example 2 e]) was reacted with [2-difluoromethyl-5-(4-trifluoromethoxy-phenyl)-2H-pyrazol-3-yl]-methanol in the presence of N,N,N',N'-tetramethyl azodicarboxamide and tributylphosphine to give {6-[2-difluoromethyl-5-(4-trifluoromethoxy-phenyl)-2H-pyrazol-3-ylmethoxy]-indol-1-yl}-acetic acid ethyl ester as white solid.

MS: 510.6 (M+H)+.

d] {6-[2-Difluoromethyl-5-(4-trifluoromethoxy-phenyl)-2H-pyrazol-3-ylmethoxy]-indol-1-yl}-acetic acid In analogy to the procedure described in example 1 f], {6-[2-difluoromethyl-5-(4-trifluoromethoxy-phenyl)-2H-pyrazol-3-ylmethoxy]-indol-1-yl}-acetic acid ethyl ester was treated with LiOH to obtain {6-[2-difluoromethyl-5-(4-trifluoromethoxy-phenyl)-2H-pyrazol-3-ylmethoxy]-indol-1-yl}-acetic acid as colorless crystals.

MS: 482.5 (M+H)+.

Example 24 a] [rac]-2-{6-[2-Methyl-5-(4-trifluoromethoxy-phenyl)-2H-pyrazol-3-ylmethoxy]-indol-1-yl}-propionic acid ethyl ester In analogy to the procedure described for example 3 c], [rac]-2-(6-hydroxy-indol-1-yl)-propionic acid ethyl ester (J. E. D. Barton, D. Cartwright, C. J. Mathews, Brit. UK Pat. Appl. (1992), GB 2253848 A1) was reacted with [2-methyl-5-(4-trifluoromethoxy-phenyl)-2H-pyrazol-3-yl]-methanol (example 11 d]) in the presence of N,N,N',N'-tetramethyl azodicarboxamide and tributylphosphine to give [rac]-2-{6-[2-methyl-5-(4-trifluoromethoxy-phenyl)-2H-pyrazol-3-ylmethoxy]-indol-1-yl}-propionic acid ethyl ester as colorless oil.

MS: 488.5 (M+H)+.

b] [rac]-2-{6-[2-Methyl-5-(4-trifluoromethoxy-phenyl)-2H-pyrazol-3-ylmethoxy]-indol-1-yl}-propionic acid In analogy to the procedure described in example 1 f], [rac]-2-{6-[2-methyl-5-(4-trifluoromethoxy-phenyl)-2H-pyrazol-3-ylmethoxy]-indol-1-yl}-propionic acid ethyl ester was treated with LiOH to obtain [rac]-2-{6-[2-methyl-5-(4-trifluoromethoxy-phenyl)-2H-pyrazol-3-ylmethoxy]-indol-1-yl}-propionic acid as off-white crystals.

MS: 460.4 (M+H)+.

Example 25 a] 5-Iodomethyl-1-methyl-3-(4-trifluoromethyl-phenyl)-1H-pyrazole

In analogy to the procedure described in example 20 a], 5-chloromethyl-1-methyl-3-(4-trifluoromethyl-phenyl)-1H-pyrazole (example 9 a]) was treated with sodium iodide in acetone to obtain 5-iodomethyl-1-methyl-3-(4-trifluoromethyl-phenyl)-1H-pyrazole as yellow solid which was used in the next step without further purification.

b] 3-[2-Methyl-5-(4-trifluoromethyl-phenyl)-2H-pyrazol-3-yl]-propionic acid ethyl ester In analogy to the procedure described in example 20 b], 5-iodomethyl-1-methyl-3-(4-trifluoromethyl-phenyl)-1H-pyrazole was reacted with ethyl acetate in the presence of lithium diisopropylamide and DMPU to obtain 3-[2-methyl-5-(4-trifluoromethyl-phenyl)-2H-pyrazol-3-yl]-propionic acid ethyl ester as yellow solid.

MS: 327.3 (M+H)+.

c] 3-[2-Methyl-5-(4-trifluoromethyl-phenyl)-2H-pyrazol-3-yl]-propan-1-ol

In analogy to the procedure described for example 1 a], 3-[2-methyl-5-(4-trifluoromethyl-phenyl)-2H-pyrazol-3-yl]-propionic acid ethyl ester was reduced with lithium aluminium hydride in diethyl ether to give 3-[2-methyl-5-(4-trifluoromethyl-phenyl)-2H-pyrazol-3-yl]-propan-1-ol as yellow oil.

MS: 285.1 (M+H)+.

d] (6-{3-[2-Methyl-5-(4-trifluoromethyl-phenyl)-2H-pyrazol-3-yl]-propoxy}-indol-1-yl)-acetic acid ethyl ester In analogy to the procedure described for example 3 c], (6-hydroxy-indol-1-yl)-acetic acid ethyl ester (example 2 e]) was reacted with 3-[2-methyl-5-(4-trifluoromethyl-phenyl)-2H-pyrazol-3-yl]-propan-1-ol in the presence of N,N,N',N'-tetramethyl azodicarboxamide and tributylphosphine to give (6-{3-[2-methyl-5-(4-trifluoromethyl-phenyl)-2H-pyrazol-3-yl]-propoxy}-indol-1-yl)-acetic acid ethyl ester as colorless oil.

MS: 486.5 (M+H)+.

e] (6-{3-[2-Methyl-5-(4-trifluoromethyl-phenyl)-2H-pyrazol-3-yl]-propoxy}-indol-1-yl)-acetic acid In analogy to the procedure described for example 1 f], (6-{3-[2-methyl-5-(4-trifluoromethyl-phenyl)-2H-pyrazol-3-yl]-propoxy}-indol-1-yl)-acetic acid ethyl ester was treated with LiOH to obtain (6-{3-[2-methyl-5-(4-trifluoromethyl-phenyl)-2H-pyrazol-3-yl]-propoxy}-indol-1-yl)-acetic acid as colorless crystals.

MS: 458.5 (M+H)+.

Example 26

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 27

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 28

Injection solutions can have the following composition:

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

Example 29

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to conventional procedures.

Example 30

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound of the formula I:

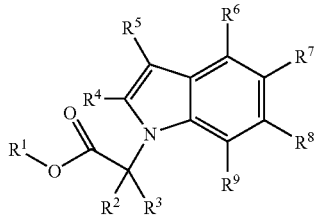

I wherein
$R^1$ is hydrogen or $C_{1-7}$-alkyl;
$R^2$ and $R^3$ independently from each other are hydrogen, $C_{1-7}$-alkyl or $C_{1-7}$-alkoxy;
$R^4$ and $R^5$ independently from each other are hydrogen, $C_{1-7}$-alkyl,
   $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
$R^6$, $R^7$, $R^8$ and $R^9$ independently from each other are hydrogen, $C_{1-7}$-alkyl,
   $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
   and one of $R^6$, $R^7$ and $R^8$ is

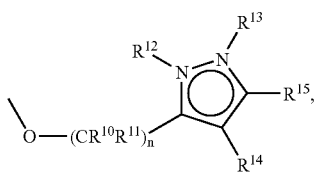

wherein
$R^{10}$ is hydrogen, $C_{1-7}$-alkyl, $C_{3-7}$-cycloalkyl or fluoro-$C_{1-7}$-alkyl;
$R^{11}$ is hydrogen, $C_{1-7}$-alkyl or $C_{1-7}$-alkoxy-$C_{1-7}$-alkyl;
one of $R^{12}$ or $R^{13}$ is hydrogen, $C_{1-7}$-alkyl, $C_{3-7}$-cycloalkyl, $C_{2-7}$-alkoxy-$C_{1-7}$-alkyl, $C_{2-7}$-alkenyl, $C_{2-7}$-alkinyl or fluoro-$C_{1-7}$-alkyl; and the other one is a lone pair;
$R^{14}$ is hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;
$R^{15}$ is aryl or heteroaryl; and
n is 1, 2 or 3; and
all enantiomers and pharmaceutically acceptable salts and/or esters thereof.

2. The compound according to claim 1, having the formula I-A:

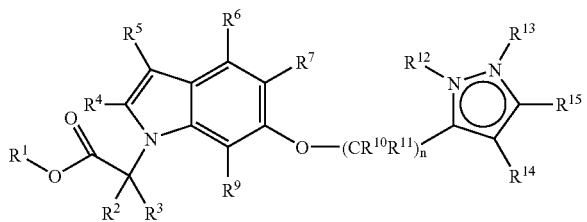

I-A wherein
$R^1$ to $R^5$, $R^{10}$ to $R^{15}$ and n are as defined in claim 1;
$R^6$, $R^7$ and $R^9$ independently from each other are hydrogen, $C_{1-7}$-alkyl,
   $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

3. The compound according to claim 2, wherein $R^6$, $R^7$ and $R^9$ are hydrogen.

4. The compound according to claim 1, having the formula I-B:

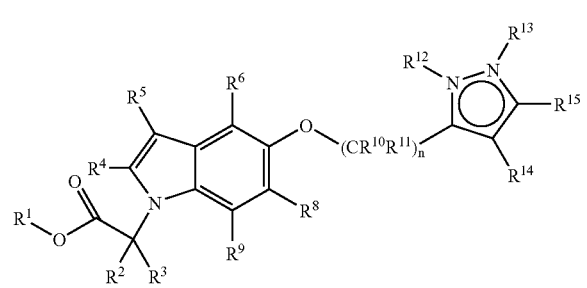

I-B wherein
$R^1$ to $R^5$, $R^{10}$ to $R^{15}$ and n are as defined in claim 1;
$R^6$, $R^8$ and $R^9$ independently from each other are hydrogen, $C_{1-7}$-alkyl,
   $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

5. The compound according to claim 4, wherein $R^6$, $R^8$ and $R^9$ are hydrogen.

6. The compound according to claim 1, having the formula I-C:

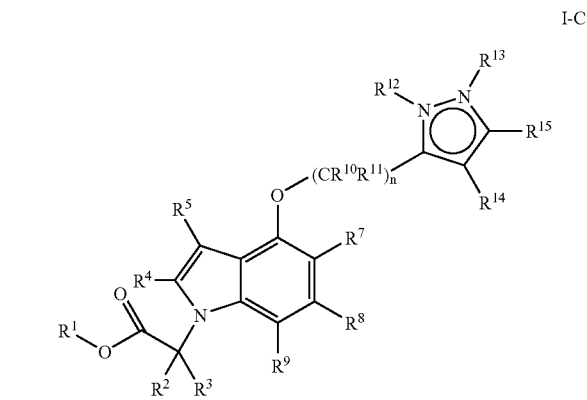

I-C wherein
$R^1$ to $R^5$, $R^{10}$ to $R^{15}$ and n are as defined in claim 1;
$R^7$, $R^8$ and $R^9$ independently from each other are hydrogen, $C_{1-7}$-alkyl,
   $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and all enantiomers and pharmaceutically acceptable salts and/or esters thereof.

7. The compound according to claim 6, wherein $R^7$, $R^8$ and $R^9$ are hydrogen.

8. The compound according to claim 1, wherein $R^1$ is hydrogen.

9. The compound according to claim 1, wherein $R^2$ and $R^3$ independently from each other are hydrogen or methyl.

10. The compound according to claim 1, wherein at least one of $R^2$ or $R^3$ is methyl.

11. The compound according to claim 1, wherein $R^4$ is hydrogen.

12. The compound according to claim 1, wherein $R^5$ is hydrogen, $C_{1-7}$-alkyl or halogen.

13. The compound according to claim 1, wherein n is 1 or 2.

14. The compound according to claim 1, wherein n is 3.

15. The compound according to claim 1, wherein one of $R^6$, $R^7$ and $R^8$ is

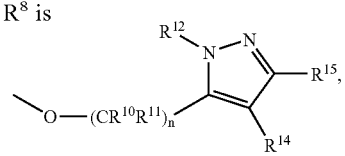

and $R^{10}$ to $R^{12}$, $R^{14}$, $R^{15}$ and n are as defined in claim 1.

16. The compound according to claim 15, wherein $R^{12}$ is $C_{1-7}$-alkyl or fluoro-$C_{1-7}$-alkyl.

17. The compound according to claim 1, wherein $R^{15}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano.

18. The compound according to claim 1, wherein $R^{15}$ is phenyl substituted with halogen, fluoro-$C_{1-7}$-alkyl or fluoro-$C_{1-7}$-alkoxy.

19. The compound according to claim 1, selected from the group consisting of:
{6-[2-methyl-5-(4-trifluoromethyl-phenyl)-2H-pyrazol-3-ylmethoxy]-indol-1-yl}-acetic acid,
(5-{2-[2-methyl-5-(4-trifluoromethyl-phenyl)-2H-pyrazol-3-yl]-ethoxy}-indol-1-yl)-acetic acid,
{6-[2,4-dimethyl-5-(4-trifluoromethyl-phenyl)-2H-pyrazol-3-ylmethoxy]-indol-1-yl}-acetic acid,
{6-[2-methyl-5-(4-trifluoromethoxy-phenyl)-2H-pyrazol-3-ylmethoxy]-indol-1-yl}-acetic acid,
{6-[2-(2,2,2-trifluoro-ethyl)-5-(4-trifluoromethyl-phenyl)-2H-pyrazol-3-ylmethoxy]-indol-1-yl}-acetic acid,
(6-{2-[2-methyl-5-(4-trifluoromethoxy-phenyl)-2H-pyrazol-3-yl]-ethoxy}-indol-1-yl)-acetic acid,
(6-{3-[2-methyl-5-(4-trifluoromethoxy-phenyl)-2H-pyrazol-3-yl]-propoxy}-indol-1-yl)-acetic acid,
{6-[2-difluoromethyl-5-(4-trifluoromethoxy-phenyl)-2H-pyrazol-3-ylmethoxy]-indol-1-yl}-acetic acid, and
(6-{3-[2-methyl-5-(4-trifluoromethyl-phenyl)-2H-pyrazol-3-yl]-propoxy}-indol-1-yl)-acetic acid.

20. The compound according to claim 1, selected from the group consisting of:
{6-[2-methyl-5-(4-trifluoromethoxy-phenyl)-2H-pyrazol-3-ylmethoxy]-indol-1-yl}-acetic acid,
{6-[2-(2,2,2-trifluoro-ethyl)-5-(4-trifluoromethyl-phenyl)-2H-pyrazol-3-ylmethoxy]-indol-1-yl}-acetic acid,
(6-{3-[2-methyl-5-(4-trifluoromethoxy-phenyl)-2H-pyrazol-3-yl]-propoxy}-indol-1-yl)-acetic acid, and
(6-{3-[2-methyl-5-(4-trifluoromethyl-phenyl)-2H-pyrazol-3-yl]-propoxy}-indol-1-yl)-acetic acid.

21. A process for the manufacture of the compound according to claim 1, comprising the steps of:

a) reacting a compound of formula

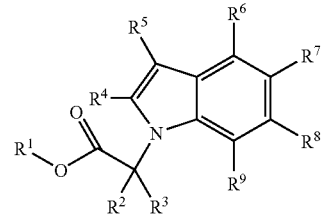

wherein $R^1$ is $C_{1-7}$-alkyl, $R^2$, $R^3$, $R^4$ and $R^5$ are as defined as in claim 1 and $R^6$, $R^7$, $R^8$ and $R^9$ are selected from hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl, and cyano with the proviso that one of $R^6$, $R^7$, or $R^8$ is —OH, with a compound of formula

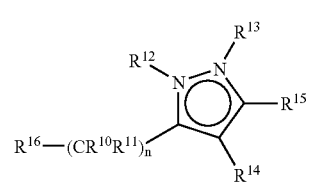

wherein X, Y, $R^{10}$, $R^{11}$, $R^{12}$, $R^{13}$, $R^{14}$, $R^{15}$ and n are as defined in claim 1 and $R^{16}$ is a leaving group, said leaving group comprising —OH, —Cl, —Br, or —I, to obtain a compound of formula

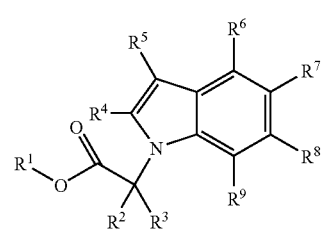

wherein $R^1$ is $C_{1-7}$-alkyl and $R^2$ to $R^9$ are defined in claim 1, and optionally hydrolysing the ester group to obtain a compound of formula I, wherein $R^1$ is hydrogen;

or, alternatively, b) reacting a compound of formula

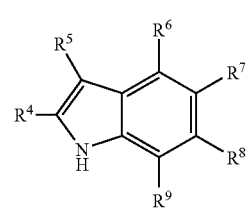

wherein $R^4$ to $R^9$ are as defined as in claim 1, with a compound of formula

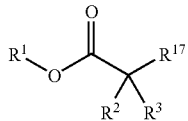
V wherein $R^1$ is $C_{1-7}$-alkyl, $R^2$ and $R^3$ are as defined in claim 1 and $R^{17}$ is a leaving group, said leaving group comprising halogen or triflate, to obtain a compound of formula

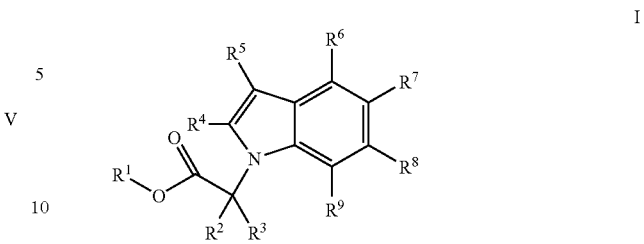
I wherein $R^1$ is $C_{1-7}$-alkyl and $R^2$ to $R^9$ are as defined in claim 1, and optionally hydrolysing the ester group to obtain a compound of formula I, wherein $R^1$ is hydrogen.

22. A pharmaceutical composition, comprising a compound according to claim 1 and a pharmaceutically acceptable carrier and/or adjuvant.

* * * * *